(12) United States Patent
Yamada et al.

(10) Patent No.: US 7,078,522 B2
(45) Date of Patent: Jul. 18, 2006

(54) PYRIDOPYRIMIDINE OR NAPHTHYRIDINE DERIVATIVE

(75) Inventors: Koichiro Yamada, Saitama-ken (JP); Masataka Hikota, Shiki (JP); Yuichi Koga, Toda (JP); Kohei Kikkawa, Kawaguchi (JP); Kenji Omori, Saitama (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 97 days.

(21) Appl. No.: 10/647,234

(22) Filed: Aug. 26, 2003

(65) Prior Publication Data

US 2005/0101615 A1    May 12, 2005

Related U.S. Application Data

(63) Continuation of application No. PCT/JP02/01638, filed on Feb. 25, 2002.

(30) Foreign Application Priority Data

Feb. 26, 2001    (JP)    ................................. 2001-49879

(51) Int. Cl.
*C07D 471/04*    (2006.01)
*C07D 519/00*    (2006.01)
*A61K 31/519*    (2006.01)
*A61P 15/10*    (2006.01)

(52) U.S. Cl. ..................... 544/117; 544/127; 544/279; 544/333; 544/350; 544/362; 546/122; 514/233.8; 514/234.2; 514/249; 514/252.16; 514/253.04; 514/256; 514/264.1; 514/264.11; 514/300

(58) Field of Classification Search ............ 514/233.8, 514/234.2, 249, 252.16, 253.04, 25, 264.1, 514/264.11, 30; 544/117, 127, 279, 333, 544/350, 362; 546/122
See application file for complete search history.

(56) References Cited

U.S. PATENT DOCUMENTS

| | | | |
|---|---|---|---|
| 3,560,624 A | 2/1971 | Rogers et al. ............... | 424/310 |
| 3,670,077 A | 6/1972 | Freeman et al. ............ | 424/200 |
| 4,060,615 A | 11/1977 | Matier et al. ................ | 424/251 |
| 4,229,456 A | 10/1980 | Bolhofer et al. ............ | 424/256 |
| 4,464,457 A | 8/1984 | Bosse et al. ................ | 430/288 |
| 4,704,459 A | 11/1987 | Todo et al. .................. | 546/123 |
| 4,959,368 A | 9/1990 | Awaya et al. ................ | 514/252 |
| 5,466,692 A | 11/1995 | Ellingboe ................... | 514/258 |
| 5,525,604 A | 6/1996 | Lee et al. .................... | 514/256 |
| 5,693,652 A | 12/1997 | Takase et al. ............... | 514/322 |
| 5,716,993 A | 2/1998 | Ozaki et al. ................ | 514/619 |
| 5,733,914 A | 3/1998 | Blankley et al. ............ | 514/258 |
| 5,817,670 A | 10/1998 | Takayama et al. .......... | 514/300 |
| 6,136,810 A | 10/2000 | Takayama et al. .......... | 514/258 |

FOREIGN PATENT DOCUMENTS

| | | |
|---|---|---|
| AU | 199955977 A1 | 5/2000 |
| DE | 2064 096 | 7/1972 |
| EP | 0 459 819 B1 | 12/1991 |
| EP | 0 668 280 A1 | 8/1995 |
| EP | 0722936 | 7/1996 |
| EP | 0 995 750 A1 | 4/2000 |
| JP | 50-95273 | 7/1975 |
| JP | 54-081299 | 6/1979 |
| JP | 2000-26294 | 1/2000 |
| JP | 2000-72751 | 3/2000 |
| WO | WO 94/28902 | 12/1994 |
| WO | WO 96/16644 | 6/1996 |
| WO | WO 96/22991 | 8/1996 |
| WO | WO 98/23597 | 6/1998 |
| WO | WO 98/33798 | 8/1998 |
| WO | WO 99/09030 | 2/1999 |
| WO | WO 00/76980 A1 | 12/2000 |
| WO | WO 01/55148 A1 | 8/2001 |
| WO | WO 01/70741 A1 | 9/2001 |
| WO | WO 03/062236 A1 | 7/2003 |

OTHER PUBLICATIONS

Perry, M.J. et al, Current Opinion in Chemical Biology, 1998, 2, 472-481.
Corbin JD, Francis SH., Int J Clin Pract. Jul.-Aug. 2002;56(6):453-9.
Cremers B, Bohm M., Herz. Jun. 2003;28(4):325-33.
Vermulapalli, S., et al., "Sildenafil relaxes rabbit clitoral corpus cavemsoum," Life Sciences, vol. 67, pp. 23-29 (2000).

(Continued)

*Primary Examiner*—Thomas C. McKenzie
(74) *Attorney, Agent, or Firm*—Finnegan, Henderson, Farabow, Garrett & Dunner, L.L.P.

(57) ABSTRACT

A pyridopyrimidine or a naphthyridine derivative of the formula (I):

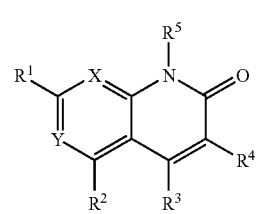

wherein $R^1$ is an optionally substituted nitrogen-containing heterocyclic group, etc.; $R^2$ is H or a lower alkyl group; $R^3$ is H or an optionally substituted lower alkyl group, etc.; $R^4$ is H, a lower alkyl group, COOH, etc.; $R^5$ is a lower alkyl group which may optionally be substituted by an optionally substituted aryl etc.; one of X and Y is CH and the other is nitrogen, or both of X and Y are nitrogen; or a pharmaceutically acceptable salt thereof, these compounds exhibiting excellent PDE V inhibitory activities, and being useful in the prophylaxis or treatment of penile erectile dysfunction, etc.

15 Claims, No Drawings

OTHER PUBLICATIONS

Watkins, C., et al., "Insulin restores neuronal nitric oxide synthase expression and function that is lost in diabetic gastrophathy," The Journal of Clinical Investigation, vol. 106, No. 3, pp. 373-384 (2000).

Bortolotti, M., et al., "Effects of Sildenafil on Esophageal Motility of Patients with Idiopathic Achalasia," Gastroenterology, vol. 118, pp. 253-257 (2000).

Mule F., et al., "Tonic Inhibitory action by nitric oxide on spontaneous mechanical activity in rat proximal colon: involvement of cyclic GMP and apamin-sensitive K channels," British Journal of Pharmacology, vol. 127, pp. 514-520 (1999).

Turner, N., et al., "Pulmonary effects of type V cyclic GMP specific phosphodiesterase inhibition in the anesthetized guinea-pig," British Journal of Pharmacology, vol. 111, pp. 1198-1204 (1994).

Bakre M., et al., "Expression and Regulation of the cGMP-Binding, cGMP-Specific Phosphodiesterase (PDE5) in Colonic Epithelial Cells: Role in the Induction of Cellular Refractoriness to the Heat-Stable Enterotoxin Peptide," Journal of Cellular Biochemistry, vol. 77, pp. 159-167 (2000).

Boolell, M., et al., "A new oral treatment for erectile dysfunction. A Double-blind, placebo controlled crossover study demonstrating dose response with rigiscan and efficacy with outpatient diary," The Journal of Urology, Supplement, vol. 155, No. 5, p. 495A 739 (1996).

Terrett, N., et al., "Sildenafil (Viagra™), a potent and selective inhibitor of type 5 CGMP phosphodiesterase with utility for the treatment of male erectile dysfunction," Bioorganic & Medicinal Chemistry Letters, vol. 6, No. 15, pp. 1819-1824 (1996).

Ballard, S., et al., "Sildenafil, a potent selective inhibitor of type 5 phosphodiesterase, enhances nitric oxide-dependent relaxation of rabbit corpus cavemosum," British Journal of Pharmacology, Proceedings Supplement, vol. 118, 153P (1996).

Goldstein, I., et al., "Oral sildenafil in the treatment of erectile dysfunction," The New England Journal of Medicine, vol. 338, No. 20, p. 1397-1404 (1998).

Goldenberg, M., "Safety and Efficacy of Sildenafil Citrate in the Treatment of Male Erectile Dysfunction," Clinical Therapeutics, vol. 20, No. 6, pp. 1033-1048 (1998).

Morales, A., et al., "Clinical safety of oral sildenafil citrate (VIAGRA™) in the treatment of erectile dysfunction," International Journal of Impotence Research, vol. 10, No. 2, pp. 69-73 (1998).

Estrade, M., et al., "Effect of a cGMP-specific phosphodiesterase inhibitor on retinal function," European Journal of Pharmacology, vol. 352, pp. 157-163 (1998).

Todd, C., et al., "Sulfilimines Derived from Sulfanilamide," Journal of American Chemical Society, vol. 65, pp. 350-355 (1943).

Grohe, K., et al., "Synthese und Reaktionen von 2,4-Dichlorpyrimidin-5-carbon-saureestem," Liebigs Ann. Chem., pp. 1025-1035 (1973).

Chan, R., et al., "The Chemistry of an Electron-Deficient 5-Deazaflavin,8-Cyano-10-methyl-5-dezaisoalloxazine," Journal of the American Chemical Society, vol. 99, No. 20, pp. 6721-6730 (1977).

Hirai, K., et al., "Heterocyclic Cation Systems . . . ," J. Org. Chem., vol. 45, pp. 253-260 (1980).

Kim, D., et al., "Synthesis of New Pyrrolidine C-Nucleosides via Staudeinger-aza-Wittig Cyclization of y-Azido Ketone," Tetrahderon Letters, 40, pp. 4825-4828 (1999).

Mertes, M., et al. "Aproaches to the Synthesis of 1-Deazauridine and 2'-Deoxy-1-deazauridine ," J. Med. Chem., vol. 10, pp. 320-325 (1967).

van Aardt, T., et al., "Direct Synthesis of Pterocarpans via Aldol Condensation of Phenylacetates with Benzaldehydes," Tetrahedron 55, pp. 11773-11786 (1999).

Yurugi, S., et al., "Studies on the Syntheses of N-Heterocyclic Compounds," Ann. Rept. Takeda Res. Lab., vol. 28, pp. 1-11 (1969).

Bolhofer, W., et al., "Inhibition of Gastric Acid Secretion by 1,8-Naphthyridin-2(1H)-ones," *J. of Med. Chem.*, vol. 22, No. 3, pp. 301-306 (1979).

P. L. Ferrarini et al., "Synthesis and antiplatelet activity of some 1,8-naphthyridine derivatives," Eur J Med Chem (1994) 29, 735-741.

PYRIDOPYRIMIDINE OR NAPHTHYRIDINE DERIVATIVE

This application is a continuation of international application number PCT/JP02/01638, filed Feb. 25, 2002, the contents of which are incorporated herein by reference and claims priority of Japanese Patent Application No. 2001-49879, filed Feb. 26, 2001.

TECHNICAL FIELD

The present invention relates to a novel pyridopyrimidine or naphthyridine derivative exhibiting a cGMP specific phosphodiesterase (PDE) inhibitory activity (PDE V inhibitory activity) and being useful as a medicament, and a process for preparing the same.

BACKGROUND ART

In general, it is known that cGMP, which is an intracellular second messenger, is decomposed and inactivated by phosphodiesterase which widely distributes in many tissues of the living body, and when said PDE activity is inactivated, the level of cGMP in cells is increased, and as a result, various pharmacological activities, for example, relaxation of vascular smooth muscle, relaxation of bronchial smooth muscle and inhibition of platelet aggregation are exhibited.

Moreover, it has been reported that such cGMP specific PDE inhibitors (i.e., PDE V inhibitors) are useful in the treatment of diseases caused by a functional disorder of cGMP-signaling, including hypertension, angina pectoris, myocardial infarction, chronic or acute heart failure, pulmonary hypertension, etc. (cf., WO 96/05176, etc.) and prostatic hyperplasia (Australian Patent Publication No. 9955977). It has also been reported that PDE V inhibitors may be useful in the treatment of female sexual dysfunction (Vemulapalli et al., Life Sciences, 67, 23–29 (2000)), diabetic gastroparesis (Watkins et al., J. Clin. Invest. 106: 373–384 (2000)), achalasia (Bortolotti et al., Gastroenterology; 118: 253–257 (2000)), diarrhea (Mule et al., Br. J. Pharmacol., 127, 514–520 (1999)), constipation (Bakre et al., J. Cell. Biochem. 77: 159–167 (2000)) and asthma (Turner et al., Br. J. Pharmacol., 111, 1198–1204 (1994)).

Furthermore, it has been also reported that 1-[4-ethoxy-3-(6,7-dihydro-1-methyl-7-oxo-3-propyl-1H-pyrazolo[4,3-d]pyrimidin-5-yl)phenylsulfonyl]-4-methyl-piperazine [general name: Sildenafil] having PDE V inhibitory activity is useful in the treatment of diseases such as penile erectile dysfunction (copulative impotence), etc. (cf., Boolell et al., The Journal of Urology, Supplement, vol. 155, no. 5, p. 495A739 (1996); Terrett et al., Bioorganic & Medicinal Chemistry Letters, vol. 6, no. 15, p. 1819 (1996); and Ballard et al., British Journal of Pharmacology, Proceeding Supplement, vol. 118, p. 153 (1996)).

However, sildenafil has been reported to have side effects such as headache, facial flushing, gut disorder, rhinitis, color sense disorder, penile erectile continuance, etc. (Irwin et al., The New England Journal of Medicine, vol. 338, no. 20, p. 1397–1404 (1998); Morales et al., International Journal of Impotence Research, vol. 10, no. 2, p. 69–73 (1998); and Goldenberg, Clinical Therapeutics, vol. 20, no. 6, p. 1033–1048 (1998)).

In addition, sildenafil has also been reported that the effects of sildenafil on light response of retina tissues and its PDE VI inhibitory activity correlate each other in the experiments on dogs (Morales et al., International Journal of Impotence Research, vol. 10, no. 2, p. 69–73 (1998)), while it has been reported that PDE VI on retina plays an important role in the sensation of light (Morrales et al., International Journal of Impotence Research, vol. 10, no. 2, p. 69–73 (1998); Estrade et al., European Journal of Pharmacology, vol. 352, p. 157–163 (1998)).

DISCLOSURE OF INVENTION

An object of the present invention is to provide a novel pyridopyrimidine or naphthyridine derivative having an excellent phosphodiesterase V (PDE V) inhibitory activity, and being useful as a remedy for the prophylaxis or treatment of penile erectile dysfunction with few side effects.

The present invention relates to a pyridopyrimidine or naphthyridine derivative of the formula (I):

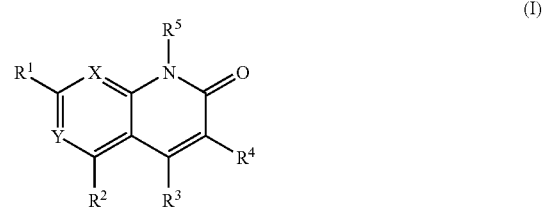

wherein $R^1$ is an optionally substituted nitrogen-containing heterocyclic group, an optionally substituted amino group or an optionally substituted alkoxy group;

$R^2$ is a hydrogen atom or a lower alkyl group;

$R^3$ is a hydrogen atom, an optionally substituted lower alkyl group or an optionally substituted heteroaryl group;

$R^4$ is a hydrogen atom, a lower alkyl group, or an optionally esterified or amidated carboxyl group;

$R^5$ is a lower alkyl group which may be optionally substituted by a group selected from an optionally substituted aryl group, an optionally substituted heteroaryl group and a di-lower alkylamino group; and one of X and Y is a group of the formula: =CH— and the other is a nitrogen atom, or X and Y are both nitrogen atoms, or a pharmaceutically acceptable salt thereof, and a process for preparing the same.

Among the compounds (I) of the present invention, the nitrogen-containing heterocyclic group of the "optionally substituted nitrogen-containing heterocyclic group" for $R^1$ includes a 5- to 10-membered monocyclic or bicyclic nitrogen-containing heterocyclic group, more particularly, a 5- or 6-membered nitrogen-containing heteromonocyclic group and a 8- to 10-membered nitrogen-containing heterobicyclic group, and most particularly, a 5- or 6-membered nitrogen-containing heteromonocyclic group such as pyrrolyl group, oxazolyl group, pyrazolyl group, pyrrolinyl group, pyrrolidinyl group, imidazolyl group, piperidyl group, piperazinyl group, morpholinyl group, pyridyl group, pyridazinyl group, pyrimidinyl group, pyrazinyl group, triazinyl group, etc. and an 8- to 10-membered nitrogen-containing heterobicyclic group such as indolyl group, isoindolyl group, indolydinyl group, quinolyl group, isoquinolyl group, purinyl group, etc.

Examples of the substituent of the "optionally substituted nitrogen-containing heterocyclic group" for $R^1$ include a lower alkyl group optionally substituted by a group selected from a hydroxy group, a halogen group and a lower alkoxy group.

Examples of the substituent of the "optionally substituted amino group" for $R^1$ include a lower alkyl group optionally substituted by a heteroaryl group, a lower alkyl group optionally substituted by an aryl group, and a lower alkoxy group, wherein the heteroaryl group includes a 5- to 6-membered aromatic nitrogen-containing heteromonocyclic group such as pyridyl group, pyrimidinyl group, etc., and the aryl group includes a 5- to 10-membered monocyclic or bicyclic aromatic hydrocarbon group such as phenyl group, naphthyl group, etc.

Examples of the substituent of the "optionally substituted lower alkoxy group" for $R^1$ include (1) an aryl group optionally substituted by a group selected from a hydroxy group, a halogen atom and a lower alkoxy group; and (2) a lower alkyl group optionally substituted by a heteroaryl group which may be optionally substituted by a group selected from a hydroxy group, a halogen atom and a lower alkoxy group, wherein the "aryl group" and the "heteroaryl group" are as defined above.

Examples or the substituent of the "optionally substituted lower alkyl group" for $R^3$ include a nitrogen-containing heterocyclic group, more specifically, those described above as specific examples of a nitrogen-containing heterocyclic group for $R^1$.

Examples of the heteroaryl group of the "optionally substituted heteroaryl group" for $R^3$ include a 5- to 10-membered aromatic nitrogen-containing-heteromonocyclic or -heterobicyclic group as defined above, wherein the substituent thereof includes a group selected from a lower alkyl group, a hydroxy group, a halogen atom and a lower alkoxy group.

Examples of the aryl group of the "optionally substituted aryl group" for $R^5$ include a 5- to 10-membered monocyclic or bicyclic aromatic hydrocarbon group as defined above, specifically phenyl group, naphthyl group, etc.

Examples of the heteroaryl group of the "optionally substituted heteroaryl group" for $R^5$ include a 5- to 6-membered aromatic nitrogen-containing heteromonocyclic group as defined above, specifically pyridyl group, pyrimidyl group, etc.

Examples of the substituent of the "optionally substituted aryl group" and the "optionally substituted heteroaryl group" for $R^5$ include a hydroxy group, a halogen atom, a lower alkoxy group, a lower alkylenedioxy group, etc.

In the definition of "optionally esterified or amidated carboxyl group" for $R^4$, examples of esterified carboxyl group include a carboxyl group esterified with a lower alkyl group, and examples of amidated carboxyl group include a carboxyl group amidated with a lower alkyl-substituted amino group which may be optionally substituted by a hydroxy group or an optionally substituted 5- to 6-membered nitrogen-containing heteromonocyclic group and a carboxyl group amidated with an optionally substituted 5- to 6-membered nitrogen-containing heteromonocyclic group. Examples of amidated carboxyl group include a carboxyl group amidated with a lower-alkyl-substituted amino group optionally substituted by a 5- to 6-membered nitrogen-containing heteromonocyclic group selected from pyrrolyl group, oxazolyl group, pyrazolyl group, pyrrolinyl group, pyrrolidinyl group, imidazolyl group, piperidyl group, piperazinyl group, morpholinyl group, pyridyl group, pyridazinyl group, pyrimidinyl group, pyrazinyl group, triazinyl group, imidazolidinyl group and thiazolyl group, each group being optionally substituted by a lower alkyl group; and a carboxyl group amidated with a 5- to 6-membered nitrogen-containing heteromonocyclic group selected from a pyrrolyl group, oxazolyl group, pyrazolyl group, pyrrolinyl group, pyrrolidinyl group, imidazolyl group, piperidyl group, piperazinyl group, morpholinyl group, pyridyl group, pyridazinyl group, pyrimidinyl group, pyrazinyl group, triazinyl group, imidazolidinyl group and thiazolyl group, each group being optionally substituted by a lower alkyl group.

Examples of the substituent of the "optionally substituted 5- or 6-membered nitrogen-containing heteromonocyclic group" include a lower alkyl group.

Throughout the present description and the claims, the "lower alkyl group" means a straight chain or branched chain alkyl group having 1 to 6 carbon atoms, such as methyl, ethyl, propyl, isopropyl, butyl, isobutyl, tert-butyl, etc. The "lower alkoxy group" means a straight chain or branched chain alkoxy group having 1 to 6 carbon atoms, such as methoxy, ethoxy, propoxy, isopropyloxy, butyloxy, isobutyloxy, tert-butyloxy, etc. The "lower alkylenedioxy group" means a straight chain or branched chain alkylenedioxy group having 1 to 6 carbon atoms, such as methylenedioxy, ethylenedioxy, trimethylenedioxy, etc.

The "halogen atom" means fluorine atom, chlorine atom, bromine atom, or iodine atom.

Preferable compounds among the compounds (I) of the present invention include a compound of the formula (I) wherein, in the definition for $R^1$, the substituent of the "optionally substituted nitrogen-containing heterocyclic group" is a lower alkyl group optionally substituted by a group selected from a hydroxy group, a halogen atom and a lower alkoxy group, the substituent of the "optionally substituted amino group" is a group selected from a lower alkyl group optionally substituted by a heteroaryl group, a lower alkyl group optionally substituted by an aryl group and a lower alkoxy group, and the substituent of the "optionally substituted lower alkoxy group" is a lower alkyl group optionally substituted by a heteroaryl group which may optionally be substituted by (1) an aryl group optionally substituted by a group selected from a hydroxy group, a halogen atom and a lower alkoxy group or (2) a lower alkyl group optionally substituted by a group selected from a hydroxy group, a halogen atom and a lower alkoxy group; in the definition for $R^3$, the substituent of the "optionally substituted lower alkyl group" is a nitrogen-containing heterocyclic group, and the substituent of the "optionally substituted heteroaryl group" is a group selected from a lower alkyl group, a hydroxy group, a halogen atom and a lower alkoxy group; in the definition for $R^5$, the substituent of the "optionally substituted aryl group" and the "optionally substituted heteroaryl group" is a group selected from a hydroxy group, a halogen atom and a lower alkoxy group; and X and Y are both nitrogen atoms.

Other preferable compounds among the compounds (I) of the present invention include a compound of the formula (I) wherein, in the definition of "lower alkyl group which may be optionally substituted by a group selected from an optionally substituted aryl group, an optionally substituted heteroaryl group and a di-lower alkylamino group" for $R^5$, the optionally substituted aryl group is a phenyl group optionally substituted by a group selected from a lower alkoxy group, a lower alkylenedioxy group and a halogen atom, and the optionally substituted heteroaryl group is a pyridyl or pyrimidyl group optionally substituted by a lower alkoxy group and/or a halogen atom.

Compounds of another preferred embodiment include a compound (I) wherein the nitrogen-containing heterocyclic group of the "optionally substituted nitrogen-containing heterocyclic group" for $R^1$ is a 5- to 6-membered nitrogen-containing heteromonocyclic group selected from pyrrolyl group, oxazolyl group, pyrazolyl group, pyrrolinyl group, pyrrolidinyl group, imidazolyl group, piperidyl group, piperazinyl group, morpholinyl group, pyridyl group, pyridazinyl group, pyrimidinyl group, pyrazinyl group and triazinyl group or an 8- to 10-membered nitrogen-containing heterobicyclic group selected from indolyl group, isoindolyl group, indolydinyl group, quinolyl group, isoquinolyl group and purinyl group; and the amidated carboxyl group of the "optionally esterified or amidated carboxyl group" for $R^4$ is a carboxyl group amidated with a lower-alkyl-substituted amino group optionally substituted by a 5- to 6-membered nitrogen-containing heteromonocyclic group selected from a pyrrolyl group, oxazolyl group, pyrazolyl group, pyrrolinyl group, pyrrolidinyl group, imidazolyl group, piperidyl group, piperazinyl group, morpholinyl group, pyridyl group, pyridazinyl group, pyrimidinyl group, pyrazinyl group, triazinyl group, imidazolidinyl group and thiazolyl group, each group being optionally substituted by a lower alkyl group, or a carboxyl group amidated with a 5- to 6-membered nitrogen-containing heteromonocyclic group selected from pyrrolyl group, oxazolyl group, pyrazolyl group, pyrrolinyl group, pyrrolidinyl group, imidazolyl group, piperidyl group, piperazinyl group, morpholinyl group, pyridyl group, pyridazinyl group, pyrimidinyl group, pyrazinyl group, triazinyl group, imidazolidinyl group and thiazolyl group, each group being optionally substituted by a lower alkyl group.

More particularly, preferable compounds of the present invention include a compound of the formula (I), wherein the nitrogen-containing heterocyclic group of the "optionally substituted nitrogen-containing heterocyclic group" for $R^1$ is a 5- or 6-membered nitrogen-containing heteromonocyclic group of the formula:

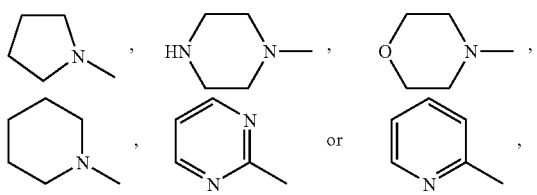

or a 8- to 10-membered nitrogen-containing heterobicyclic group of the formula:

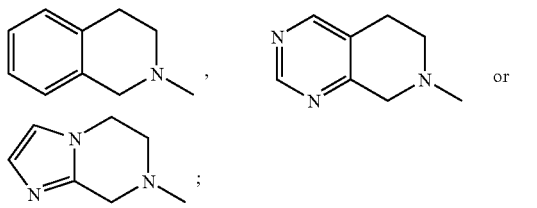

and the "optionally esterified or amidated carboxyl group" for $R^4$ is a carboxyl group amidated with a group selected from a lower alkyl-substituted amino group which may be optionally substituted by a group of the formula:

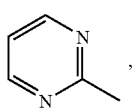

an amino group optionally substituted by a group of the formula:

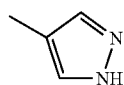

which may be optionally substituted by a lower alkyl group, and a group of the formula:

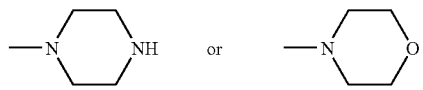

which may be optionally substitute by a lower alkyl group.

More particularly, preferable compounds of the present invention include a compound of the formula (I) wherein the "optionally substituted nitrogen-containing heterocyclic group" for $R^1$ is a group of the formula:

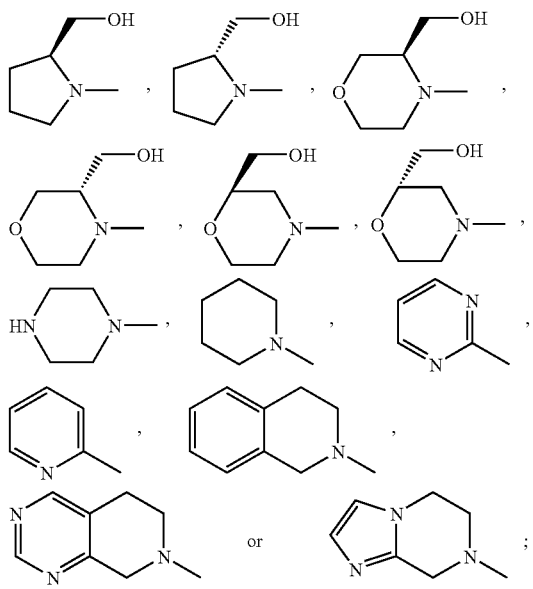

and the "optionally esterified or amidated carboxyl group" for $R^4$ is a carboxyl group amidated with a group selected from a lower alkyl-substituted amino group optionally substituted by a group of the formula:

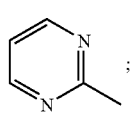

an amino group optionally substituted by a group of the formula:

and a group of the formula:

More preferable compounds of the present invention include a compound of the formula (I) wherein $R^1$ is a group selected from the formulas:

$R^2$ is a hydrogen atom;
$R^3$ is a hydrogen atom;
$R^4$ is a hydroxy group or a carboxyl group amidated with a lower alkyl-substituted amino group optionally substituted by a group of the formula:

or an amino group optionally substituted by a group of the formula:

and $R^5$ is a lower alkyl group substituted by a phenyl group optionally substituted by a lower alkoxy group and/or a halogen atom.

Especially preferable compounds include a compound of the formula (I) wherein $R^1$ is a group selected from the formulas:

$R^2$ is a hydrogen atom;
$R^3$ is a hydrogen atom;
$R^4$ is a carboxyl group amidated with an amino group optionally substituted by a group of the formula:

and $R^5$ is a lower alkyl group optionally substitute by phenyl group which may optionally be substituted by a lower alkoxy group and/or a halogen atom.

Among the compounds (I) of the present invention, pharmaceutically preferable compounds include a compound selected from the following group or a pharmaceutically acceptable salt thereof:

(S)-2-(2-Hydroxymethyl-1-pyrrolidinyl)-5-[2-(4-morpholinyl)ethyl]-8-(3-chloro-4-methoxybenzyl)-7,8-dihydro-7-oxo-pyrido[2,3-d]pyrimidine;

(S)-2-(2-Hydroxymethyl-1-pyrrolidinyl)-6-[N-{4-(1,3,5-trimethyl)pyrazolyl}carbamoyl]-8-(3-chloro-4-methoxybenzyl)-7,8-dihydro-7-oxo-pyrido[2,3-d]pyrimidine;

(S)-2-(2-Hydroxymethyl-1-pyrrolidinyl)-8-(3-chloro-4-methoxybenzyl)-7,8-dihydro-7-oxo-pyrido[2,3-d]pyrimidine; and (S)-2-(2-Hydroxymethyl-1-pyrrolidinyl)-5-methyl-8-(3-chloro-4-methoxybenzyl)-7,8-dihydro-7-oxo-pyrido[2,3-d]pyrimidine.

Among the compounds (I) of the present invention, (S)-2-(2-hydroxymethyl-1-pyrrolidinyl)-6-[N-{4-(1,3,5-trimethyl)pyrazolyl}carbamoyl]-8-(3-chloro-4-methoxybenzyl)-7,8-dihydro-7-oxo-pyrido[2,3-d]pyrimidine or a pharmaceutically acceptable salt thereof is pharmaceutically more preferable compound.

The present invention also provides a pyridopyrimidine or a naphthyridine derivative of the formula (VIII):

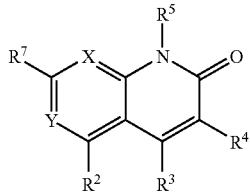

(VIII)

wherein $R^7$ is a halogen atom or a group of the formula:

—$SR^9$ wherein $R^9$ is an optionally substituted lower alkyl group or an optionally substituted aryl group;
$R^2$ is a hydrogen atom or a lower alkyl group;
$R^3$ is a hydrogen atom, an optionally substituted lower alkyl group or an optionally substituted heteroaryl group;
$R^4$ is a hydrogen atom, a lower alkyl group, or an optionally esterified or amidated carboxyl group;
$R^5$ is a lower alkyl group which may be optionally substituted by a group selected from an optionally substituted aryl group, an optionally substituted heteroaryl group and a di-lower alkylamino group; and one of X and Y is a group of the formula: =CH— and the other is a nitrogen atom, or X and Y are both nitrogen atoms, or a salt thereof, and a compound of the formula:

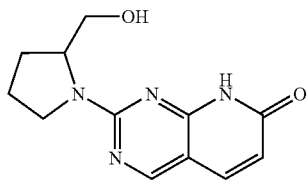

or a salt thereof, which are useful as an intermediate for preparing the compound of the formula (I) above.

When the compound (I) of the present invention or a pharmaceutically acceptable salt thereof, or a compound (VIII) or a salt thereof has an asymmetric carbon atom at $R^1$, $R^2$, $R^3$, $R^4$, $R^5$ and/or $R^7$, it may exist in the form of an optically active isomer thereof owing to said asymmetric carbon atom, and the present invention also includes these optical isomers and a mixture thereof.

The present compound (I) can clinically be used either in the free form or in the form of a pharmaceutically acceptable salt thereof. The pharmaceutically acceptable salt of the compound (I) includes a salt with an inorganic acid, such as hydrochloride, sulfate, nitrate or hydrobromide, or a salt with an organic acid such as acetate, fumarate, oxalate, citrate, methanesulfonate, benzenesulfonate, tosylate, or maleate.

The present compound (I) or a salt thereof includes either intramolecular salt or an additive thereof, and solvates or hydrates thereof.

The present compound (I) or a pharmaceutically acceptable salt thereof can be administered either orally or parenterally, and can be formulated into a conventional pharmaceutical preparation such as tablets, granules, fine granules, pills, capsules, powders, injections, inhalants, buccal preparations, sublingual tablets, syrups, dry syrups, jellies, suppositories, ointments, elixirs, liniments, lotions, drinks, nasal drops, percutaneous preparations, and rapidly-disintegrating tablets in oral cavity, etc. These pharmaceutical preparations may be prepared by formulating a compound of the present invention with a pharmaceutically acceptable additive such as excipient, binder, wetting agent, disintegrator, thickening agent, etc., by a conventional method.

The dose of the compound (I) of the present invention or a pharmaceutically acceptable salt thereof may vary in accordance with the administration route, and age, weight and conditions of a patient. For example, when administered in an injection preparation, it is usually in the range of about 0.001–100 mg/kg/day, preferably in the range of about 0.1–10 mg/kg/day. When administered in an oral preparation, it is usually in the range of about 0.1–200 mg/kg/day, preferably in the range of about 0.1–80 mg/kg/day.

Concomitantly, since the compound (I) of the present invention or a pharmaceutically acceptable salt thereof exhibits an excellent selective PDE V inhibitory activity, it also may be useful in the prophylaxis or treatment of diseases caused by a functional disorder of cGMP-signaling, such as pulmonary hypertension, diabetic gastroparesis, hypertension, angina pectoris, myocardial infarction, chronic or acute heart failure, female sexual dysfunction, prostatic hyperplasia, asthma, diarrhea, constipation and achalasia in addition to the above-mentioned erectile dysfunction.

BEST MODE FOR CARRYING OUT THE INVENTION

The compounds (I) of the present invention may be prepared by the following PROCESSes [A] to [G].

[PROCESS A]

Among the compounds (I) of the present invention, a compound wherein $R^4$ is a hydrogen atom or a lower alkyl group, which is shown by the formula (I-1):

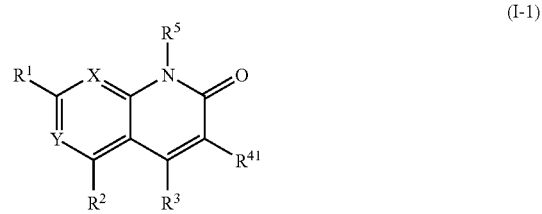

(I-1)

wherein $R^{41}$ is a hydrogen atom or a lower alkyl group, and the other symbols are as defined above can be prepared by reacting a compound of the formula (II):

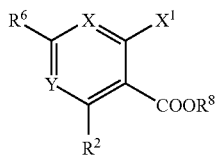

(II)

wherein $X^1$ is a halogen atom, $R^6$ is an optionally substituted nitrogen-containing heterocyclic group, an optionally substituted amino group, an optionally substituted lower alkoxy group, a halogen atom or a group of the formula: —$SR^9$ (wherein $R^9$ is an optionally substituted lower alkyl group or an optionally substituted aryl group), $R^8$ is a protecting group for carboxyl group, and the other symbols are as defined above, with a compound of the formula (1):

(1)

wherein the symbol is as defined above to give a compound of the formula (III):

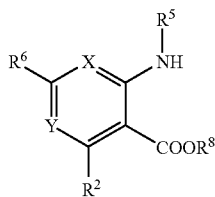

(III)

wherein the symbols are as defined above, reducing the compound (III) to give a compound of the formula (IV):

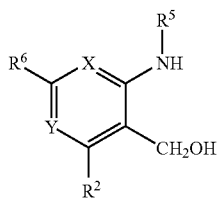

(IV)

wherein the symbols are as defined above, oxidizing the compound (IV) to give a compound of the formula (V):

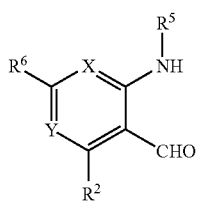

(V)

wherein the symbols are as defined above, and if necessary, reacting the compound (V) with a metal salt of a compound of the formula (2):

(2)

wherein $R^{31}$ is an optionally substituted lower alkyl group or an optionally substituted heteroaryl group to give a compound of the formula (VI):

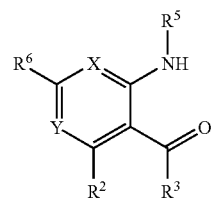

(VI)

wherein the symbols are as defined above, further reacting the compound (VI) with a compound of the formula (3):

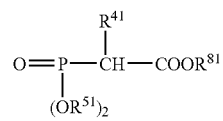

(3)

wherein $R^{51}$ is a lower alkyl group, $R^{81}$ is a protecting group for carboxyl group and other symbols are as defined above to give a compound of the formula (VII):

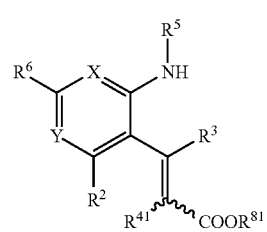

(VII)

wherein the symbols are as defined above, cyclizing the compound (VII) to give a compound of the formula (VIII-1):

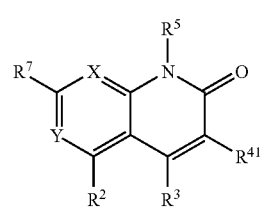

(VIII-1)

wherein $R^7$ is a halogen atom or a group of the formula: —$SR^9$ (wherein $R^9$ is an optionally substituted lower alkyl group or an optionally substituted aryl group), and the other symbols are as defined above, and, (a) when $R^7$ is a halogen atom, reacting the compound (VIII-1) with a compound of the formula (4):

$$R^1\text{—H} \quad (4)$$

wherein the symbol is as defined above; and (b) when $R^7$ is a group of the formula: —$SR^9$, that is, when the compound (VIII-1) is a compound of the formula (VIII-2):

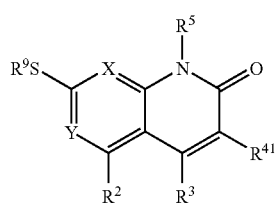

(VIII-2)

wherein the symbols are as defined above, oxidizing the compound (VIII-2) to give a compound of the formula (IX):

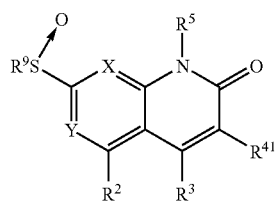

(IX)

wherein the symbols are as defined above, followed by reacting the compound (IX) with a compound of the formula (4).

[PROCESS B]

The compound (I-1) can also be prepared by reacting a compound of the formula (II) with ammonia to give a compound of the formula (III'):

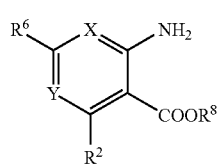

(III')

wherein the symbols are as defined above, reducing the compound (III') to give a compound of the formula (IV'):

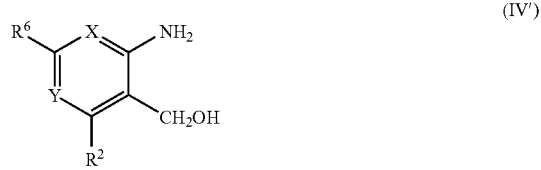

(IV')

wherein the symbols are as defined above, oxidizing the compound (IV') to give a compound of the formula (V'):

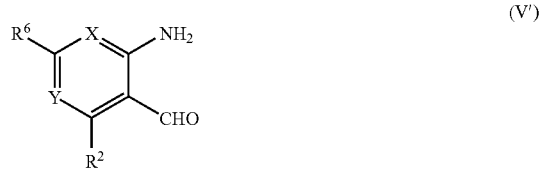

(V')

wherein the symbols are as defined above, and, if necessary, reacting the compound (V') with a compound (2), followed by reacting the resultant compound with a compound (3) to give a compound of the formula (VII'):

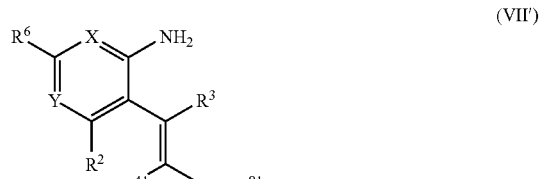

(VII')

wherein the symbols are as defined above, cyclizing the compound (VII') to give a compound of the formula: (VIII-3):

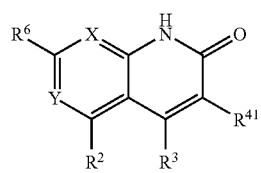

(VIII-3)

wherein the symbols are as defined above, reacting the compound (VIII-3) with a compound of the formula (5):

$$R^5\text{—}X^2 \quad (5)$$

wherein $X^2$ is a halogen atom and the other symbol is as defined above, and reacting the resulting compound wherein $R^6$ is a halogen atom with a compound (4), or oxidizing the resulting compound wherein $R^6$ is a group of the formula: $-SR^9$ to give a compound (IX), and reacting the compound (IX) with a compound (4).

[PROCESS C]

Among the compounds (I) of the present invention, a compound wherein $R^4$ is an optionally esterified or amidated carboxyl group, which is shown by the formula (I-2):

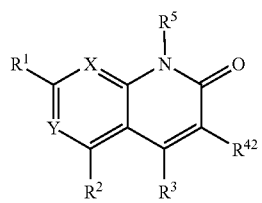

(I-2)

wherein $R^{42}$ is an optionally esterified or amidated carboxyl group and the other symbols are as defined above can be prepared by reacting a compound of the formula (VI) with a di-lower alkyl malonate or a malonic acid, cyclizing the resultant compound, followed by hydrolysis, and then re-esterification or re-amidation, to give a compound of the formula (VIII-4):

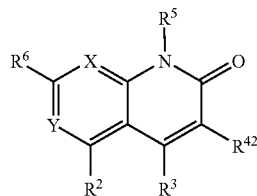

(VIII-4)

wherein the symbols are as defined above, and, in the case of a compound (VIII-4) wherein $R^6$ is a halogen atom, reacting the compound with a compound of the formula (4), and in the case of a compound (VIII-4) wherein $R^6$ is a group of the formula: $-SR^9$, oxidizing the compound and then reacting with a compound of the formula (4). The group $R^{42}$ on the resultant compound (I-2) may be hydrolyzed in a conventional manner, and re-esterified or re-amidated.

[PROCESS D]

Furthermore, among the compounds of the formula (I), a compound (I) wherein $R^4$ is an optionally substituted ethyl group can be prepared by reacting a compound (V) with the compound (6):

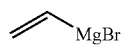

(6)

oxidizing the resultant compound to give a compound of the formula (X):

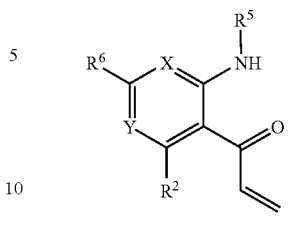

(X)

wherein the symbols are as defined above, reacting the compound (X) with a compound of the formula (7):

$$R^{33}-H \tag{7}$$

wherein $R^{33}$ is a substituent on the ethyl group of $R^3$ and the other symbols are as defined above to give a compound of the formula (XI):

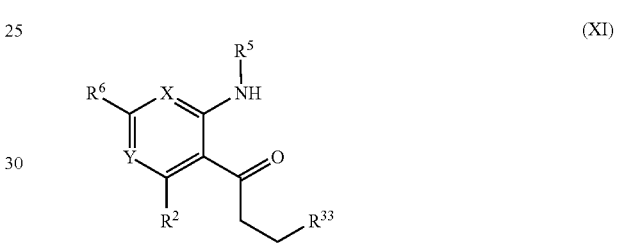

(XI)

wherein the symbols are as defined above, and reacting the compound (XI) with a compound of the formula:

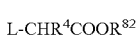

$$L-CHR^4COOR^{82} \tag{8}$$

wherein L is a leaving group, $R^{82}$ is a protecting group for carboxyl group and the other symbols are as defined above.

[PROCESS E]

A compound (I-1) wherein $R^3$ is an optionally substituted lower alkyl group or an optionally substituted heteroaryl group can be prepared by cyclizing a compound of the formula (VII) or (VII') wherein $R^3$ is a hydrogen atom through the reaction with a metallic derivative of compound (2), followed by oxidation for converting the $R^3$ into an optionally substituted lower alkyl group or an optionally substituted heteroaryl group.

[PROCESS F]

When the group $R^2$ and/or $R^3$ of a compound of the formula (I-1) is a hydrogen atom, said $R^2$ and/or $R^3$ can be converted into a group other than hydrogen atom by reacting the compound (I-1) with a metallic derivative of compound (2) followed by oxidation.

[PROCESS G]

The compound of the formula (I-1) can also be prepared by first preparing a compound of the formula (VI) in the same manner as that described in PROCESS A, and in the case wherein the resultant compound is shown by the formula (VI-1):

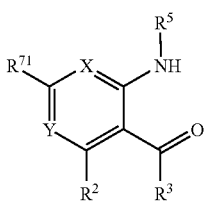

(VI-1)

wherein $R^{71}$ is a halogen atom or a group of the formula: —$SR^9$ (wherein $R^9$ is as defined above), and the other symbols are as defined above, and, furthermore, (a) when $R^{71}$ is a halogen atom, reacting the compound (VI-1) with the above-mentioned compound (4); or (b) when $R^{71}$ is a group: —$SR^9$, that is, the resultant compound is a compound of the formula (VI-2):

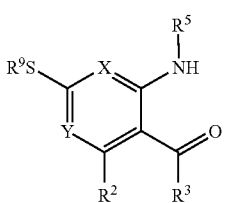

(VI-2)

wherein the symbols are as defined above, oxidizing the compound (VI-2) to give a compound of the formula (XII):

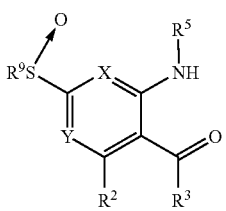

(XII)

wherein the symbols are as defined above, reacting the compound (XII) with the compound (4) to give a compound of the formula (XIII):

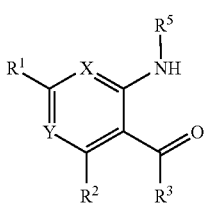

(XIII)

wherein the symbols are as defined above, reacting the compound (XIII) with the above-mentioned compound (3) to give a compound of the formula (XIV):

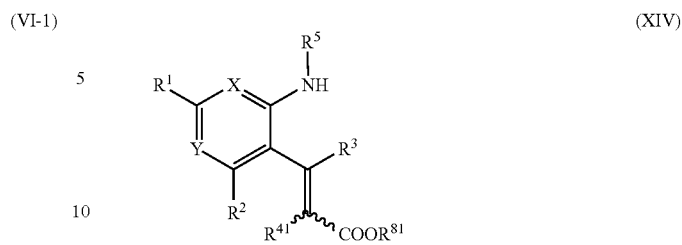

(XIV)

wherein the symbols are as defined above, and cyclizing the compound (XIV).

The above PROCESSes A to G can be carried out as follows.

[PROCESS A]

The reaction of the compound (III) with the compound (1) can be carried out in the presence or absence of an acid scavenger in a solvent. The acid scavenger includes, for example, an organic base such as N,N-diisopropylethylamine, N-methylmorpholine, triethylamine, pyridine, etc., and an inorganic base such as sodium hydride, sodium carbonate, potassium carbonate, sodium hydrogen carbonate, etc. The solvent may be any solvent which does not disturb the reaction, for example, dimethylsulfoxide, tetrahydrofuran, toluene, ethyl acetate, chloroform, dimethoxyethane, xylene, N,N-dimethylformamide, etc. The reaction is carried out at a temperature of −10° C. to a boiling point of the solvent to be used, preferably at a temperature of 0° C. to room temperature.

The reaction of reducing the compound (III) to give the compound (IV) can be carried out in the presence of a reducing agent in a suitable solvent. The reducing agent is preferably an alkali metal aluminum hydride such as lithium aluminum hydride, and an alkali metal borohydride such as lithium borohydride, etc. The solvent may be any solvent which does not disturb the reaction, for example, tetrahydrofuran, dioxane, diethyl ether, dimethoxyethane, etc. The reaction is carried out at a temperature of −78° C. to a boiling point of the solvent to be used, preferably at a temperature of −10° C. to room temperature.

The reaction of oxidizing the compound (IV) to give the compound (V) can be carried out in the presence of an oxidizing agent in a solvent. The oxidizing agent may be any agent which can convert an alcohol into a carbonyl compound, for example, manganese dioxide, barium permanganate, potassium permanganate, 2,3-dichloro-5,6-dicyano-1,4-benzoquinone, pyridinium chlorochromate, pyridinium dichloromate, etc. The solvent may be any solvent which does not disturb the reaction, for example, chloroform, toluene, ethyl acetate, 1,2-dichloroethane, methylene chloride, tetrahydrofuran, etc. The reaction is carried out at a temperature of 0° C. to 100° C., preferably at a temperature of room temperature to 70° C.

The reaction of the compound (V) with a metal salt of compound (2) to give the compound (VI) can be carried out in a suitable solvent. The metal salt of compound (2) is preferably lithium salt, etc. The solvent may be any solvent which does not disturb the reaction, for example, tetrahydrofuran, dioxane, diethyl ether, dimethoxyethane, etc. The reaction may preferably proceed at a temperature of −78° C. to room temperature.

The reaction of the compound (VI) with the compound (3) to give the compound (VII) can be carried out in the presence of a base in a solvent. Examples of the base include sodium hydride, potassium tert-butoxide, potassium carbonate, sodium carbonate, sodium methoxide, sodium ethoxide, potassium hydroxide, sodium hydroxide, lithium hydroxide, potassium amide, lithium amide, lithium diisopropylamide, etc. The solvent may be any solvent which does not disturb the reaction, for example, tetrahydrofuran, methanol, ethanol, dimethoxyethane, dioxane, N,N-dimethylformamide, dimethylsulfoxide, diethyl ether, dimethoxyethane, dioxane, toluene, etc. The reaction may carried out at a temperature of −78° C. to a boiling point of the solvent to be used, preferably at a temperature of −10° C. to 60° C.

The cyclization of the compound (VII) can be carried out in the presence of a basic catalyst in a solvent. Examples of the basic catalyst include sodium hydroxide, potassium hydroxide, lithium hydroxide, sodium methoxide, sodium ethoxide, potassium tert-butoxide, sodium hydride, etc. The solvent may be any solvent which does not disturb the reaction, for example, methanol, ethanol, tetrahydrofuran, dimethylsulfoxide, N,N-dimethylformamide, etc. The reaction may be carried out at a temperature of 0° C. to a boiling point of the solvent to be used, preferably at a temperature from room temperature to 100° C.

The reaction of oxidizing the compound (VIII-2) to give the compound (IX) is carried out in the presence of an oxidizing agent in a solvent. The oxidizing agent includes, for example, peracids such as m-chloroperbenzoic acid, peracetic acid, etc., and an inorganic oxidizing agent such as manganese dioxide, sodium periodate, hydrogen peroxide, dinitrogen tetroxide, halogen, hydroperoxide, iodobenzene acetate, t-butyl hypochlorite, sulfuryl chloride, potassium peroxymonosulfate, etc. The solvent may be any solvent which does not disturb the reaction, for example, chloroform, methylene chloride, dichloroethane, acetic acid, etc. The reaction is carried out at a temperature of −78° C. to 50° C., preferably from −10° C. to 10° C.

The reaction of the compound (VIII-1) or (IX) with the compound (4) to give the compound (I-1) can be carried out in the presence or absence of an acid scavenger in a solvent. The acid scavenger includes, for example, an organic base such as N,N-diisopropylethylamine, N-methylmorpholine, triethylamine, pyridine, etc., and an inorganic base such as sodium hydride, sodium carbonate, potassium carbonate, sodium hydrogen carbonate, etc. The salt of the compound (4) is preferably an alkali metal salt such as sodium salt, potassium salt, etc. The solvent may be any solvent which does not disturb the reaction, for example, N,N-dimethylformamide, tetrahydrofuran, dimethoxyethane, dimethylsulfoxide, etc. The reaction is carried out at a temperature of 0° C. to 150° C., preferably at a temperature of room temperature to 60° C.

[PROCESS B]

The reaction of the compound (II) with ammonia to give the compound (III') can be carried out in the same manner as in the reaction of the compound (II) with the compound (I) in PROCESS A above.

The reduction of the compound (III') to give the compound (IV') can be carried out in the same manner as in the reaction of reducing the compound (III) to give the compound (IV) in PROCESS A above.

The oxidation of the compound (IV') to give the compound (V') can be carried out in the same manner as in the reaction of oxidizing the compound (IV) to give the compound (V) in PROCESS A above.

The reaction of the compound (V') with the compound (2) and the following reaction with the compound (3) to give the compound (VII') can also be carried out in the same manner as in the reaction of the compound (V) with the compound (2) and the following reaction of the compound (VI) with the compound (3) in PROCESS A above.

The cyclization of the compound (VII') to give the compound (VIII-3) can also be carried out in the same manner as in the cyclization of the compound (VII) to give the compound (VIII-1), as mentioned above.

The reaction of the compound (VIII-3) with the compound (5) can be carried out in the presence of an acid scavenger in a solvent. The acid scavenger includes, for example, potassium carbonate, sodium carbonate, cesium carbonate, potassium hydroxide, sodium hydroxide, sodium hydride, potassium hydride, sodium methoxide, sodium ethoxide, potassium t-butoxide, etc. The solvent may be any solvent which does not disturb the reaction, for example, N,N-dimethylformamide, N,N-dimethylacetamide, dimethylsulfoxide, toluene, tetrahydrofuran, dioxane, etc. The reaction proceeds preferably at a temperature of −10° C. to a boiling point of the solvent used, preferably at a temperature of room temperature to 60° C.

The oxidation of a compound wherein $R^6$ is a —$SR^9$ among the reaction products can be carried out in the same manner as in the reaction of oxidizing the compound (VIII-2) to give the compound (IX) in PROCESS A above. Furthermore, the reaction wherein the compound (4) is reacted with either the reaction product of the reaction between the compound (VIII-3) and the compound (5) or the compound (IX), which is obtained by oxidizing said reaction product, to give the compound (I-1) can be carried out in the same manner as in the reaction wherein the compound (4) is reacted with either the compound (VIII-1) or the compound (IX) to give the compound (I-1) in the PROCESS A above.

[PROCESS C]

The reaction of the compound (VI) with a di-lower alkyl malonate or malonic acid can be carried out in the presence of a base in a solvent. The reaction can be facilitated by the addition of a catalytic amount of acid. Examples of the base include an organic base such as piperidine, pyridine, diethylamine, triethylamine, etc., and an inorganic base such as sodium methoxide, etc. The acid to be added at a catalytic amount includes hydrochloric acid, acetic acid, benzoic acid, titanium tetrachloride, etc. The solvent may be any solvent which does not disturb the reaction, for example, methanol, ethanol, benzene, toluene, acetonitrile, propionitrile, tetrahydrofuran, carbon tetrachloride, etc. The reaction proceeds preferably at a temperature of −50° C. to 200° C., preferably from 0° C. to a boiling point of the solvent to be used. The following cyclization to give the compound (VIII-4) preferably proceeds in situ at a temperature of 50° C. to a boiling point of the solvent to be used.

The oxidation of the product can be carried out in the same manner as in the reaction of oxidizing the compound (VIII-2) to give the compound (IX) in PROCESS A above, and the reaction wherein a reaction product between the compound (IV) and malonic acid, etc. or an oxidation product of said reaction product is reacted with the compound (4) to give the compound (I-2) can be carried out in the same manner as in the reaction of the compound (VIII-1) or the compound (IX) with the compound (4) to give the compound (I-1) in PROCESS A above.

[PROCESS D]

The reaction of the compound (V) with the compound (6) can be carried out in an appropriate solvent. Examples of preferred solvent includes tetrahydrofuran, dioxane, diethyl ether, etc. The reaction proceeds preferably at a temperature of −78° C. to 60° C., preferably at a temperature of −78° C. to room temperature. Then, the reaction of oxidizing the product to give the compound (X) can be carried out in the presence of an oxidizing agent in a solvent. The oxidizing agent may be any one which can convert an alcohol into a carbonyl compound, for example, manganese dioxide, barium permanganate, potassium permanganate, 2,3-dichloro-5,6-dicyano-1,4-benzoquinone, pyridinium chlorochromate, pyridinium dichloromate, etc. The solvent may be any solvent which does not disturb the reaction, for example, chloroform, toluene, ethyl acetate, 1,2-dichloroethane, methylene chloride, tetrahydrofuran, etc. The reaction is carried out at a temperature of 0° C. to 100° C., preferably at a temperature of room temperature to 70° C.

The reaction of the compound (X) with the compound (7) can be carried out in the presence or absence of a base in a solvent. Examples of the base include an organic base such as N,N-diisopropylethylamine, N-methylmorpholine, triethylamine, pyridine, etc., and an inorganic base such as sodium hydride, sodium carbonate, potassium carbonate, sodium hydrogen carbonate, etc. Examples of the solvent include ethanol, N,N-dimethylformamide, tetrahydrofuran, dimethoxyethane, dimethylsulfoxide, etc. The reaction proceeds preferably at a temperature of 0° C. to 150° C., preferably at a temperature of room temperature to 60° C.

The reaction of the compound (XI) with the compound (8) can be carried out in the presence of a base in a solvent. The leaving group L of the compound (8) includes a trialkylsilyl group, trialkyl- or triaryl-phosphonyl group, etc. Examples of the base include sodium hydride, sodium methoxide, sodium ethoxide, lithium hydroxide, triethylamine, potassium hexamethylsilazide, lithium diisopropylamide, lithium dicyclohexylamide, etc. The solvent may be any solvent which does not disturb the reaction, for example, tetrahydrofuran, dimethylsulfoxide, toluene, methanol, N,N-dimethylformamide, benzene, dimethoxyethane, tetrahydroethylenediamine, etc. The reaction preferably proceeds at a temperature of −100° C. to a boiling point of the solvent to be used, preferably from −78° C. to 30° C.

[PROCESS E]

The reaction of a compound of the formula (VII) or (VII') wherein $R^3$ is a hydrogen atom with a metallic derivative of compound (2) for cyclization can be carried out in an appropriate solvent. Examples of the metallic derivative of compound (2) include a compound which can be prepared from a metal salt of compound (2) and copper cyanide. The solvent may be any solvent which does not disturb the reaction, for example, ether, tetrahydrofuran, dioxane, toluene, benzene, ethanol, etc. The reaction preferably proceeds at a temperature of −100° C. to 50° C., preferably at a temperature of −80° C. to room temperature The oxidation of the resultant compound can be carried out in the presence of an oxidizing agent in a solvent. Examples of preferred oxidizing agent include manganese dioxide, 2,3-dichloro-5,6-dicyano-p-benzoquinone, chloranile, selenium dioxide, oxygen (air), etc. The solvent may be any solvent which does not disturb the reaction, for example, chloroform, carbon tetrachloride, acetonitrile, N,N-dimethylformamide, p-cinone, xylene, toluene, benzene, dioxane, tetrahydrofuran, nitrobenzene, pyridine, acetic acid, etc. The reaction preferably proceeds at a temperature of −20° C. to the boiling point of the solvent to be used, preferably at a temperature of room temperature to 100° C.

[PROCESS F]

The reaction of the compound (I-1) (wherein $R^2$ and/or $R^3$ is a hydrogen atom) with a metallic derivative of compound (2), and the oxidation of the resultant compound can be carried out in the same manner as in the reaction wherein a metallic derivative of compound (2) is reacted and the resultant compound is oxidized in the PROCESS E above.

[PROCESS G]

The reaction of the compound (VI-1) with the compound (4) can be carried out in the same manner as in the reaction of the compound (VIII-1) with the compound (4) in the PROCESS A above.

The reaction of oxidizing the compound (VI-2) can be carried out in the same manner as in the reaction of oxidizing the compound (VIII-2) in the PROCESS A above.

The reaction of the compound (XII) with the compound (4) can be carried out in the same manner as in the reaction of the compound (IX) with the compound (4) in the PROCESS A above.

The reaction of the compound (XIII) with the compound (3) can be carried out in the same manner as in the reaction of the compound (VI) with the compound (3) in the PROCESS A above.

The cyclization of the compound (XIV) can be carried out in the same manner as in the cyclization of the compound (VII).

The thus obtained compound (I) can be, if necessary, converted into the pharmaceutically acceptable salts thereof.

Among the starting compounds (II), compounds wherein $R^2$ is a hydrogen atom and $R^6$ is a group of the formula: —$SR^9$ can be prepared in accordance with the method described in the Journal of the American Chemical Society, page 350, vol. 65, 1943. Besides, compounds of the formula (II) wherein $R^6$ is an optionally substituted nitrogen-containing heterocyclic group, an optionally substituted amino group, or an optionally substituted lower alkoxy group can be prepared by reacting a compound of the formula (II) wherein $R^6$ is a halogen atom with the compound (4). Furthermore, compounds (II) wherein $R^2$ is a lower alkyl group can be prepared in accordance with the method described in Justus Leibigs Annalen der Chemie, 1973, (5–6), 1025–1035, or DE 2 064 096.

Examples of the compound (I) of the present invention which can be prepared by the above-exemplified processes are illustrated below, but the present invention should not be construed to be limited thereto.

EXAMPLE 1

(S)-2-(2-Hydroxymethyl-1-pyrrolidinyl)-8-(3-chloro-4-methoxybenzyl)-7,8-dihydro-7-oxo-pyrido[2,3-d]pyrimidine

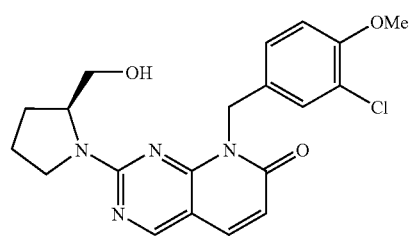

(1) To a solution of 2-methylthio-4-chloro-5-ethoxy-carbonylpyrimidine (25.33 g) in N,N-dimethylformamide (85 ml) are added a solution of 3-chloro-4-methoxybenzylamine (19.62 g) in N,N-dimethylformamide (15 ml) and triethylamine (16.7 ml) under ice-cooling. The mixture is stirred at room temperature for 20 minutes, and thereto is added 3-chloro-4-methoxybenzylamine (940 mg), and the mixture is further stirred for 15 minutes. To the mixture is further added said amine (940 mg), and the mixture is stirred for another 15 minutes. The reaction mixture is poured into a mixture of ice water and citric acid, and extracted with ethyl acetate. The extract is washed successively with a 10% aqueous citric acid solution, water and brine, and dried over anhydrous sodium sulfate. The solvent is distilled off under reduced pressure, and the residue is washed with n-hexane to give 2-methylthio-4-(3-chloro-5-methoxybenzylamino)-5-ehoxy-carbonylpyrimidine (38.34 g). M.p. 86° C.

(2) To a suspension of lithium aluminum hydride (4.15 g) in tetrahydrofuran (150 ml) is added a solution of 2-methylthio-4-(3-chloro-4-methoxybenzylamino)-5-ethoxycarbonylpyrimidine (38.32 g) in tetrahydrofuran (100 ml) under ice-cooling at temperature ranging from 5° C. to 10° C. over a period of 1 hour. After the addition is completed, the ice bath is removed, and the reaction mixture is stirred at room temperature for 1 hour. To the reaction mixture is added water (4.15 ml) under ice-cooling, and thereto is further added 3N aqueous sodium hydroxide solution (4.15 ml). To the mixture is added water (4.15 ml) three times, and the mixture is stirred at room temperature for 1 hour. The reaction mixture is treated with magnesium sulfate, and the solid precipitates are collected by filtration and washed with tetrahydrofuran. The filtrate and the washings are combined, concentrated under reduced pressure, and triturated with a mixture of ethyl acetate and isopropyl ether. The resulting crystals are collected by filtration, and washed thoroughly with isopropyl ether to give 2-methylthio-4-(3-chloro-4-methoxybenzylamino)-5-hydroxymethylpyrimidine as pale yellow crystalline powder:

First crop: yield, 25.10 g; m. p. 162–163° C.
Second crop: yield, 2.32 g; m. p. 159–160° C.

The above solid precipitates are washed again with isopropyl ether, and the filtrate is concentrated under reduced pressure to give colorless crystals. The resulting solids are suspended in isopropyl ether, filtered, and the precipitates are washed thoroughly with isopropyl ether and hexane to give 2-methylthio-4-(3-chloro-4-methoxybenzylamino)-5-hydroxymethylpyrimidine (4.26 g) as colorless crystals, m.p. 161–162° C.

(3) To a suspension of 2-methylthio-4-(3-chloro-4-methoxybenzylamino)-5-hydroxymethylpyrimidine (25.10 g) obtained in (2) above in chloroform (150 ml) is added manganese dioxide powder (37.6 g), and the mixture is vigorously stirred at room temperature for 1 day. To the mixture is further added manganese dioxide powder (12.6 g, 0.5-fold amount of the starting compound), and the mixture is stirred for three nights. The insoluble materials are quickly removed by filtration through celite, and the filtrate is concentrated under reduced pressure. The residue is suspended in a mixture of ethyl acetate and isopropyl ether. The precipitates are filtered, and washed successively with isopropyl ether and hexane to give 2-methylthio-4-(3-chloro-4-methoxybenzylamino)-5-formylpyrimidine (22.43 g) as colorless crystals, m.p. 124–125° C.

(4) A solution of 2-methylthio-4-(3-chloro-4-methoxybenzylamino)-5-formylpyrimidine (2.057 g) in chloroform (20 ml) is treated with m-chloroperbenzoic acid (80%, 1.468 g) at 0° C. for 30 minutes. To the reaction mixture are is added L-prolinol (0.901 g), and then triethylamine (1.33 ml), and the mixture is reacted at 0° C. for 1 hour.

The reaction mixture is warmed to room temperature, and diluted with ethyl acetate. The mixture is washed successively with a saturated aqueous sodium hydrogen carbonate solution, water and a saturated brine and dried over anhydrous sodium sulfate. The precipitates are removed by filtration through a silica plug. The filtrate is concentrated under reduced pressure to give (S)-2-(2-hydroxymethyl-1-pyrrolidinyl)-4-(3-chloro-4-methoxybenzylamino)-5-formylpyrimidine (1.9990 g) as colorless amorphous. MS (m/z): 377 (MH$^+$).

(5) A solution of methyl diethylphosphonoacetate (0.084 g) in dry tetrahydrofuran (2.0 ml) is treated with sodium hydride (60% suspension in oil, 9.9 mg) at 0° C. for 30 minutes, which emits hydrogen gas quickly and gives a clear solution. To the solution is added (S)-2-(2-hydroxymehyl-1-pyrrolidinyl)-4-(3-chloro-4-methoxybenzylamino)-5-formylpyrimidine (aldehyde, 0.100 g) in tetrahydrofuran, and the mixture is stirred at room temperature for 2 hours. To the mixture are added a saturated aqueous sodium hydrogen carbonate solution and ethyl acetate. The ethyl acetate layer is separated, washed with water and saturated brine, purified by preparative TLC (solvent; hexane:ethyl acetate=1:1), and triturated with ethyl acetate and diisopropyl ether to give (S)-2-(2-hydroxymethyl-1-pyrrolidinyl)-4-(3-chloro-4-methoxybenzylamino)-5-(methoxycarbonylvinyl)pyrimidine (15.3 mg) as a pale yellow solid. M.p. 163–164° C. IR(nujol): 3380, 1707, 1597, 1556, 1500, 1463, 1193, 1174 cm$^{-1}$. MS (m/z): 433(MH$^+$, base peak), 401.

(6) A mixture of the compound (45.0 mg) obtained in (5) above, 1 N aqueous sodium hydroxide solution(0.31 ml) and methanol(2 ml) is stirred at room temperature overnight, followed by reflux for 5 hours. After cooling, the reaction mixture is washed with diethyl ether. The aqueous layer is acidified with citric acid, and sodium chloride (solid) is added to the aqueous layer. The organic layer is separated, dried over sodium sulfate, filtered, and concentrated in vacuo. The resultant residue is purified by preparative TLC (solvent; chloroform:methanol=5:1), concentrated, triturated with diisopropyl ether and ethyl acetate to give (S)-2-(2-hydroxymethyl-1-pyrrolidinyl)-8-(3-chloro-4-methoxybenzyl)-7,8-dihydro-7-oxo-pyrido [2,3-d]pyrimidine (8.8 mg) as a colorless solid.

M.p.: 142–143° C.; MS (m/z): 401(MH$^+$, base peak).

EXAMPLE 2

2-(2-Pyridylmethoxy)-8-(3-chloro-4-methoxybenzyl)-7,8-dihyro-7-oxo-pyrido[2,3-d]pyrimidine

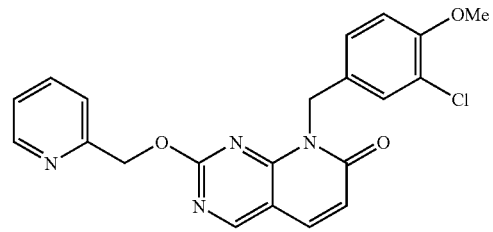

(1) A suspension of sodium hydride (60% suspension in oil, 0.556 g) in dry tetrahydrofuran (60 ml) is treated with trimethyl phosphonoacetate (2.25 ml) at 0° C. To the precipitated colorless salts is added tetrahydrofuran (20 ml), and the mixture is stirred at 0° C. for 30 minutes. After addition of 2-methylthio-4-(3-chloro-4-methoxybenzylamino)-5-formylpyrimidine (3.000 g) obtained in EXAMPLE 1 (2) above in one portion, tetrahydrofuran (10 ml) is added thereto to dissolve the precipitated salts. The colorless reaction mixture turns yellow by addition of aldehyde compound. After addition of ethyl acetate and water to the reaction mixture, the organic layer is separated, washed with saturated brine, and dried over anhydrous sodium sulfate. The resulting residue is purified by silica gel column chromatography (solvent; hexane:ethyl acetate=3:1 followed by chloroform alone) to give 2-methylthio-4-(3-chloro-4-methoxybenzylamino)-5-(methoxycarbonylvinyl)pyrimidine (2.827 g) as a pale yellow solid. M.p. 144–144.5° C.

(2) The compound (2.827 g) obtained in (1) above is treated with sodium hydride (35 mg) in methanol (50 ml) for 1.5 hours under reflux. After cooling the reaction mixture, the precipitates are collected by filtration. The resultant crystals are washed successively with methanol and diisopropyl ether to give 2-methylthio-8-(3-chloro-4-methoxybenzylamino)-7,8-dihydro-7-oxo-pyrido[2,3-d]pyrimidine (2.490 g) as colorless fine powder. M.P. 189–190° C., MS (m/z): 530(MH$^+$, base peak).

IR(nujol): 1735, 1694, 1583, 1553, 1503, 1439, 1260, 1143, 1028 cm$^{-1}$.

(3) A mixture of the compound (0.500 g) obtained in (2) above, m-chloroperbenzoic acid (0.311 g) and chloroform (7 ml) is allowed to react at room temperature for 5 minutes. The solvent is distilled off under reduced pressure and the residue is dissolved in ethyl acetate. The precipitates are washed and dissolved in chloroform. The chloroform solution is washed with a saturated aqueous sodium hydrogen carbonate solution, dried over sodium sulfate, filtered, and concentrated in vacuo. The residue is triturated with ethyl acetate to give 2-methylsulfonyl-8-(3-chloro-4-methoxybenzylamino)-7,8-dihydro-7-oxo-pyrido[2,3-d]pyrimidine (0.520 g) as a brown solid. M.P. 212–214° C.

IR(nujol): 1673, 1557, 1504, 1455, 1362, 1292, 1257, 1142, 1071, 800 cm$^{-1}$. MS (m/z): 364(MH$^+$, base peak), 332(MH$^+$–32).

(4) A solution of 2-pyridinemethanol (54 mg) in tetrahydrofuran (3 ml) is treated with sodium hydride (19.8 mg) at room temperature for 1 hour. To the resultant suspension of sodium salt is added the compound (150 mg) obtained in (3) above in one portion. The mixture is stirred at room temperature for 2 hours. After addition of a saturated aqueous sodium hydrogen carbonate solution and ethyl acetate, the organic layer is separated, washed with water and saturated brine and dried over sodium sulfate. Purification by silica gel chromatography gives colorless oil, which is recrystallized from a mixture of ethyl acetate and diisopropyl ether to give the objective 2-(2-pyridylmethoxy)-5-(3-chloro-4-methoxybenzyl)-7,8-dihyro-7-oxo-pyrido[2,3-d]pyrimidine (78.8 mg). M.p. 130–131° C.

IR(nujol): 1665, 1584, 1505, 1265, 1040, 803 cm$^{-1}$. MS (m/z): 409(MH$^+$, base peak).

EXAMPLE 3

(S)-2-(2-Hydroxymethyl-1-pyrrolidinyl)-8-N-mehyl-7,8-dihydro-7-oxo-pyrido[2,3-d]pyrimidine

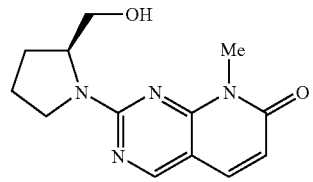

(1) To a solution of 2-methylthio-4-chloro-5-ethoxycarbonylpyrimidine (10.0 g) in tetrahydrofuran (150 ml) is added 28% aqueous ammonia (30 ml) to obtain emulsion. The emulsion is changed to a clear solution by adding methanol (about 20 ml), and stirred at room temperature overnight. The reaction mixture is concentrated in vacuo and extracted with ethyl acetate. The organic layer is washed successively with water (×2) and brine, dried over sodium sulfate, concentrated in vacuo to give a colorless solid. The solid is recrystallized from ethyl acetate (high temperature, about 100 ml) to give 2-methylthio-5-ethoxycarbonyl-4-aminopyrimidine (7.00 g) as colorless prism crystals. M.p. 131–132° C., MS (m/z): 214 (MH$^+$).

IR(nujol): 3412, 3269, 3133, 1693, 1630, 1567, 1367, 1311, 1206, 1096 cm$^{-1}$.

(2) To an emulsion of lithium aluminum hydride (664 mg) in tetrahydrofuran (35 ml) is added dropwise the compound (3.55 g) obtained in (1) above in tetrahydrofuran (35 ml) in an ice bath over 30 minutes. The whole reaction solution is stirred for another 30 minutes. To the reaction solution are added water (0.66 ml) and then 3N aqueous sodium hydroxide solution (0.66 ml) to obtain a gel-like gray suspension. After stirring for a while, the mixture is treated again with water (3×0.66 ml=2 ml), and stirred for 2 hours. The mixture is filtered through a magnesium sulfate bed, and the precipitates are washed thoroughly with tetrahydrofuran. The filtrates are combined and concentrated in vacuo to obtain a colorless solid. The solid is suspended in a mixed solvent of ethyl acetate and diisopropyl ether, and the precipitated crystals are collected by filtration, washed thoroughly with diisopropyl ether and hexane to give 2-methylthio-5-hydroxymethyl-4-aminopyrimidine (2.56 g) as colorless crystalline powder. M.p. 129° C., MS (m/z): 172 (MH$^+$), 154(—H$_2$O).

IR(nujol): 3438, 3289, 3134, 1637, 1547, 1524, 1480, 1466, 1356, 1267 cm$^{-1}$.

(3) To a suspension of the compound (2.52 g) obtained in (2) above in chloroform (70 ml) is added manganese dioxide powder (7.56 g), which is three-fold amount compared to the starting material, and the mixture is stirred vigorously at room temperature overnight. The insoluble substances are removed by filtration, and the filtrate is concentrated in vacuo to obtain a colorless solid, which is extremely insoluble in an organic solvent. The resultant solid is recrystallized from a mixed solution of chloroform and methanol, triturated with a mixed solvent of chloroform-diisopropyl ether-hexane, washed with diisopropyl ether and hexane to give 2-methylthio-5-formyl-4-aminopyrimidine (1.75 g) as colorless powder. M.p. 186–187° C., MS (m/z): 170 (MH$^+$).

IR(nujol): 3406, 3289, 3177, 1667, 1631, 1616, 1585, 1529, 1387, 1180, 781 cm$^{-1}$.

(4) To a suspension of sodium hydride (60% suspension in oil, 130 mg) in dry tetrahydrofuran (15 ml) is added trimethyl phosphonoacetate (526 µl) in an ice bath. During the addition, insoluble salts separate out. The reaction mixture is stirred at the same temperature for 30 minutes. To the suspension is added powdery compound (500 mg) obtained in (3) above in one portion in the ice bath. The ice bath is removed and the inhomogeneous mixture is stirred vigorously to obtain a clear solution in a few minutes. After addition of ethyl acetate and water at room temperature, the organic layer is separated, washed with brine, dried over sodium sulfate, and concentrated in vacuo to obtain a colorless solid. The solid is suspended in a mixture of ethyl acetate and diisopropyl ether, filtered, and washed with diisopropyl ether and hexane to give 2-methylthio-5-(methoxycarbonylvinyl)-4-aminopyrimidine (619 mg) as slightly yellow crystalline powder. M.p. 192–196° C., MS (m/z): 226 (MH$^+$).

IR(nujol): 3446, 3302, 1706, 1644, 1624, 1573, 1381, 1329, 1167 cm$^{-1}$.

(5) To a suspension of the compound (610 mg) obtained in (4) above in methanol (12 ml) is added sodium hydride (60%, 130 mg), and the mixture is refluxed for 1 hour. The reaction solution is neutralized with aqueous 2N hydrochloride solution. The mixture is diluted with water, and precipitated solids are collected, washed with water, ether, and hexane to give 2-methylthio-7,8-dihydro-7-oxo-pyrido[2,3-d]pyrimidine (481 mg) as powder. M.p. 270–271° C., MS (m/z): 194 (MH$^+$).

IR(nujol): 1672, 1608, 1597, 1525, 1460, 1383, 1167 cm$^{-1}$.

(6) To a suspension of the compound (103 mg) obtained in (5) above in dry dimethylformamide (3 ml) is added iodomethyl (37 µl) in ice bath using microsyringe, followed by addition of potassium carbonate powder (81 mg) in one portion. The reaction mixture is stirred at 0° C. for 30 minutes, and then at room temperature for 30 minutes. After addition of water to the reaction mixture, the mixture is extracted with ethyl acetate. The organic layer is washed successively with water and brine, dried over sodium sulfate, and concentrated in vacuo to give a colorless solid. The resultant crude product is suspended in a mixed solvent of ethyl acetate and diisopropyl ether. The solids are collected by filtration, washed with a mixture of diisopropyl ether and hexane to give 2-methylthio-8-N-methyl-7,8-dihydro-7-oxo-pyrido[2,3-d]pyrimidine (82 mg) as colorless powder. M.p. 192–193° C., MS (m/z): 208(MH$^+$).

IR(nujol): 1677, 1569, 1459, 1369, 1173 cm$^{-1}$.

(7) To a solution of the compound (70 mg) obtained in (6) above in chloroform (1.5 ml) is added m-chloroperbenzoic acid (70%, 92 mg) in an ice-bath in one portion, and the mixture is stirred for 20 minutes. A solution of L-prolinol (38 mg) and triethylamine (103 mg) in chloroform (0.5 ml) is reacted with the reaction mixture, and stirred for 3 hours at room temperature. After addition of water, and then potassium carbonate, the organic layer is separated, dried over sodium sulfate, and concentrated in vacuo to give a mixture of yellow oil and white solid (crude, 106 mg). The residue is suspended in a mixture of ethyl acetate and diisopropyl ether, and slightly yellow solids are collected by filtration, washed thoroughly with a mixture of diisopropyl ether and hexane to give (S)-2-(2-hydroxymethyl-1-pyrrolidinyl)-8-N-methyl-7,8-dihydro-7-oxo-pyrido[2,3-d]pyrimidine (65 mg). M.p. 143–144° C., MS (m/z): 261 (MH$^+$).

IR(nujol): 3336, 3275, 1647, 1611, 1574, 1517, 1463, 1413, 1341, 1049 cm$^{-1}$.

EXAMPLE 4

(S)-2-(2-Hydroxymethyl-1-pyrrolidinyl)-6-(methoxycarbonyl)-8-(3-chloro-4-methoxybenzyl)-7,8-dihydro-7-oxo-pyrido[2,3-d]pyrimidine

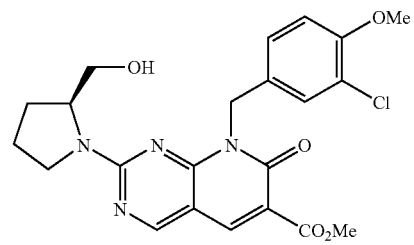

(1) A mixture of 2-methylthio-5-formyl-4-(3-chloro-4-methoxybenzylamino)pyrimidine(0.7000 g), dimethyl malonate (7 ml), piperidine (214 µl) and acetic acid (248 µl) is stirred at room temperature for 1 hour, followed by stirring at 120° C. for 4 hours. The reaction mixture is cooled, diluted with ethyl acetate, washed with a saturated aqueous sodium hydrogen carbonate solution and saturated brine, dried over sodium sulfate, and filtered. The filtrate is concentrated in vacuo and the residue is triturated with diisopropyl ether and ethyl acetate to give 2-methylthio-8-(3-chloro-4-methoxybenzyl)-6-(methoxycarbonyl)-7,8-dihydro-7-oxo-pyrido[2,3-d]pyrimidine (0.6819 g) as yellow powder. M.p. 191–193° C.

IR(nujol): 1749, 1698, 1672, 1613, 1578, 1529, 1503, 1413, 1364, 1331, 1289, 1259, 1179, 800 cm$^{-1}$. MS (m/z): 406 (MH$^+$, base peak).

(2) A solution of the compound (0.846 g) obtained in (1) above in chloroform (8 ml) is treated with m-chloroperbenzoic acid (70%, 0.513 g) at room temperature for 30 minutes with stirring. To the mixture are added triethylamine (0.435 ml) and L-prolinol (0.232 g), and the mixture is stirred for three nights. The reaction mixture is diluted with ethyl acetate, washed with a saturated aqueous sodium hydrogen carbonate solution and saturated brine, and dried over sodium sulfate. Purification by silica gel column chromatography (solvent; chloroform:ethyl acetate=6:1→ethyl acetate alone) gives yellow powder, which is then triturated with a mixture of ethyl acetate and diisopropyl ether to give (S)-2-(2-hydroxymethyl-1-pyrrolidinyl)-6-methoxycarbonyl-8-(3-chloro-4-methoxybenzyl)-7,8-dihydro-7-oxo-pyrido[2,3-d]pyrimidine (21.5 mg) as yellow powder. M.p. 175–176° C.

EXAMPLE 5

(S)-2-(2-Hydroxymethyl-1-pyrrolidinyl)-6-methyl-8-(3-chloro-4-methoxybenzyl)-7,8-dihydro-7-oxo-pyrido[2,3-d]pyrimidine

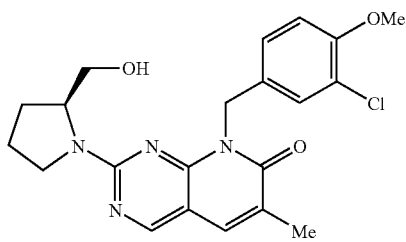

(1) A mixture of 2-methylthio-5-formyl-4-(3-chloro-4-methoxybenzylamino)pyrimidine (0.2000 g), triethyl 2-phosphonopropionate (0.441 g), sodium hydride (60% suspension in oil, 74.1 mg) and dry tetrahydrofuran (5 ml) is stirred at room temperature for 1 hour. The solvent is evaporated in vacuo and the residue is used in the next step without purification.

A solution of the residue obtained in the above in chloroform (5 ml) is treated with m-chloroperbenzoic acid (70%, 168 mg) at room temperature for 15 minutes. To the mixture are added L-prolinol (69 mg) and triethylamine (172 μl), followed by stirring overnight at room temperature. Purification by silica gel chromatography (solvent; chloroform:ethyl acetate=1:1) gives 2-methylsulfinyl-5-(2-ethoxycarbonyl-1-propenyl)-6-(3-chloro-4-methoxybenzylamino)pyridine (about 0.20 g) as colorless oil.

The so obtained 2-methylsulfinyl-5-(2-ethoxycarbonyl-1-propenyl)-6-(3-chloro-4-methoxybenzylamino)pyridine (0.20 g), L-prolinol (69 mg), triethylamine (172 μl) and chloroform (5 ml) are refluxed for 6 hours. Purification by silica gel chromatography gives (S)-2-(2-hydroxymethyl-1-pyrrolidinyl)-5-(2-ethoxycarbonyl-1-propenyl)-6-(3-chloro-4-methoxybenzylamino)pyridine (about 200 mg).

(2) A mixture of the compound (about 200 mg) obtained in (1) above, sodium hydride (60% suspension in oil, 17.4 mg) and methanol (2 ml) is refluxed for 6 hours. Unreacted starting materials are recovered by silica gel column chromatography. A solution of the recovered starting materials in chloroform is mixed with silica gel, and volatile substances are removed in vacuo. The residue is allowed to stand for 24 hours. The product is recovered by washing with a mixture of chloroform and methanol (10:1).

The so recovered starting materials are treated in the same manner as described above, except that silica gel (Merck; 60 g) is used.

After separation with preparative TLC (chloroform:methanol=20:1), preparative TLC is repeated two times to obtain a fraction rich in lactam compounds. From this fraction, (S)-2-(2-hydroxymethyl-1-pyrrolidinyl)-6-methyl-8-(3-chloro-4-methoxybenzyl)-7,8-dihydro-7-oxo-pyrido[2,3-d]pyrimidine (30.7 mg) is recovered as a colorless solid (partially crystallized).

IR(film): 3383, 1653, 1589, 1520, 1502, 1458, 1446, 1257, 1063.5, 799, 751 cm$^{-1}$. MS (m/z): 415(MH$^+$, base peak).

EXAMPLE 6

(S)-2-(2-Hydroxy-1-pyrrolidinyl)-4-methyl-8-(3-chloro-4-methoxybenzyl)-7,8-dihydro-7-oxo-pyrido[2,3-d]pyrimidine

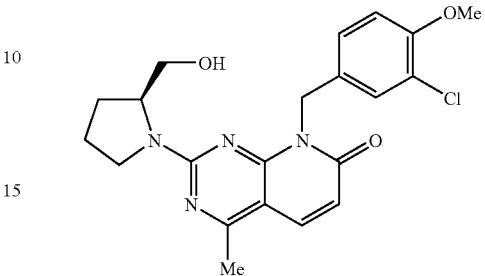

(1) To a suspension of copper iodide (133 mg) in diethyl ether (1.4 ml) is added dropwise 1.1M solution of methyl lithium in diethyl ether (1.27 ml) at temperature ranging from −15° C. to −20° C. over 20 minutes, when the color of the reaction solution turns yellow to give a yellow suspension. The suspension changes to colorless clear solution with the addition of methyl lithium. The resultant solution is stirred for 15 minutes, and thereto added tetrahydrofuran (2 ml), followed by addition of a solution of 2-methylthio-7-oxo-8-(3-chloro-4-methoxybenzyl)-7,8-hydropyrido[2,3-d]pyrimidine (50.0 mg) in tetrahydrofuran (4 ml). The reaction mixture is warmed with stirring so that temperature is gradually elevated from −20° C. to room temperature over 4 hours.

The reaction mixture is poured into a saturated aqueous sodium hydrogen carbonate solution and ethyl acetate is added thereto. The precipitates obtained are filtered and the filter cake is washed with ethyl acetate. The filtrate and washings are combined, washed with saturated brine, purified by silica gel column chromatography (solvent; chloroform:ethyl acetate=3:1), and triturated to give 2-methylthio-4-methyl-8-(3-chloro-4-methoxybenzyl)-3,4,7,8-tetrahydro-7-oxo-pyrido[2,3-d]pyrimidine (26.0 mg) as bright yellow powder. M.p. 184–186° C.

IR(nujol): 3172, 1635, 1572, 1466, 1295, 1253, 1162, 1066, 809 cm$^{-1}$. MS (m/z): 364 (MH$^+$, base peak).

(2) A mixture of the compound (70.0 mg) obtained in (1) above, manganese dioxide (0.35 g) and chloroform (5 ml) is stirred at room temperature for 3 days. After addition of manganese dioxide (0.35 g), stirring is continued overnight. The mixture is filtered to remove insoluble materials, and purified by silica gel column chromatography to give 2-methylthio-4-methyl-8-(3-chloro-4-methoxybenzyl)-7,8-dihydro-7-oxo-pyrido[2,3-d]pyrimidine (31.9 mg) as a colorless solid.

(3) To a solution of the compound (31.9 mg) obtained in (2) above in chloroform (3 ml) is added m-chloroperbenzoic acid (19.0 mg), and the mixture is reacted at room temperature for 15 minutes. After addition of L-prolinol (8.6 mg) and triethylamine (21.4 μl), reaction is continued at room temperature for 3 days. The reaction solution is subjected to silica gel column chromatography equilibrated with hexane:ethyl acetate (1:1) eluting with hexane:ethyl acetate (2:1) to give colorless oil. The oil is then crystallized from a mixture of diisopropyl ether and ethyl acetate to give (S)-2-(2-hydroxymethyl-1-pyrrolidinyl)-4-methyl-8-(3-chloro-4-methoxybenzyl)-7,8-dihydro-7- oxo-pyrido[2,3-d]pyrimidine (28.7 mg) as colorless crystalline powder. M.p. 152–153° C.

IR(nujol): 3355, 1653, 1640, 1600, 1571, 1527, 1503, 1343, 1262, 1047, 826, 799 cm$^{-1}$. MS (m/z): 415(MH$^+$, base peak).

EXAMPLE 7

(S)-2-(2-Hydroxy-1-pyrrolidinyl)-5-methyl-8-(3-chloro-4-methoxybenzyl)-7,8-dihydro-7-oxo-pyrido[2,3-d]pyrimidine

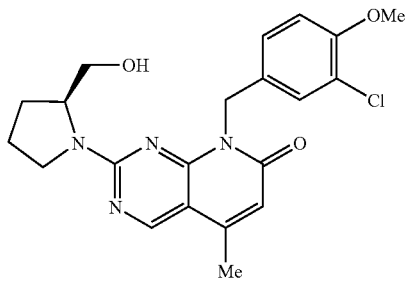

(1) Trimethyl phosphonoacetate (940 μl) is added to a suspension of sodium hydride (60%, 232 mg) in tetrahydrofuran (45 ml) at 0° C. The mixture is stirred at 0° C. for 1 hour, while colorless salts precipitate. To the mixture is added 2-methylthio-5-formyl-4-(3-chloro-4-methoxybenzylamino)pyrimidine (1.50 g) in one portion and the mixture is stirred at 0° C. for 1 hour. After addition of ethyl acetate and water, the organic layer is washed with brine, and dried over sodium sulfate. Sodium sulfate is removed by filtration, and the filtrate is concentrated in vacuo. The residue is purified by silica gel column chromatography (silica gel; 50 g, solvent; chloroform:ethyl acetate=3:1) to give 2-methylthio-5-(methoxycarbonylvinyl)-4-(3-chloro-4-methoxybenzylamino)pyrimidine (1.74 g) as colorless crystals. M.p. 141–142.5° C. MS (FAB): 380 (MH$^+$).

IR(nujol): 1714, 1629 cm$^{-1}$.

(2) A 1.1M solution of methyl lithium in diethyl ether (5.98 ml) is added dropwise to a suspension of copper cyanide (294 mg) in diethyl ether (2 ml) at −78° C., and the mixture is stirred at 0° C. for 1.5 hours, when the mixture turns to a pale yellow solution. To the reaction mixture is then added a solution of the compound (250 mg) obtained in (1) above in tetrahydrofuran (10 ml) at −78° C. The mixture is warmed to 0° C. and mixed at 0° C. for another 1 hour. After addition of a mixture of saturated aqueous ammonium chloride solution and aqueous ammonia (1:1), the mixture is extracted with ethyl acetate. The extract is washed with brine and dried over sodium sulfate.

Sodium sulfate is removed by filtration and the filtrate is concentrated in vacuo. The residue is purified by silica gel column chromatography (silica gel, 25 g; solvent, hexane: ethyl acetate=2:1) to give 2-methylthio-5-methyl-8-(3-chloro-4-methoxybenzylamino)-5,6,7,8-tetrahydro-7-oxo-pyrido[2,3-d]pyrimidine (107 mg) as light brown crystals. M.p. 118–120.5° C. MS (APCI): 396 (MH$^+$+CH$_3$OH).

(3) A mixture of the compound (85 mg) obtained in (2) above, m-chloroperbenzoic acid (63 mg) and chloroform (3 ml) is stirred at 0° C. for 1 hour. After addition of L-prolinol (28 mg) and triethylamine (48 mg), the mixture is stirred at room temperature for 3 hours. L-prolinol (24 mg) is added again, and the mixture is stirred at room temperature for 1.5 hours, and then at 60° C. for 9 hours. Prolinol (72 mg) is further added and the mixture is stirred at 60° C. for 1.5 days.

Water is added to the reaction mixture, and the organic layer is washed with brine and dried over sodium sulfate. Sodium sulfate is removed by filtration, and the filtrate is concentrated in vacuo. The residue is purified by column chromatography (silica gel, 20 g; solvent, ethyl acetate) to give (S)-2-(2-hydroxymethyl-1-pyrrolidinyl)-5-methyl-8-(3-chloro-4-methoxybenzylamino)-5,6,7,8-tetrahydro-7-oxo-pyrido[2,3-d]pyrimidine (73 mg) as colorless amorphous. MS(APCI): 417 (MH$^+$).

IR(nujol): 1693, 1601, 1551, 1503 cm$^{-1}$.

(4) The compound obtained in (3) above is treated with 2,3-dichloro-5,6-dicyano-1,4-benzoquinone in dioxane at room temperature for 3 days, and then at 60° C. for 10 hours to give (S)-2-(2-hydroxymethyl-1-pyrrolidinyl)-5-methyl-8-(3-chloro-4-methoxybenzyl)-7,8-dihydro-7-oxo-pyrido[2,3-d]pyrimidine. M.p. 150–153° C.

EXAMPLE 8

(S)-2-(2-Hydroxymethyl-1-pyrrolidinyl)-2-methyl-6-methoxycarbonyl-8-(3-chloro-4-methoxybenzyl)-7,8-dihydro-7-oxo-pyrido[2,3-d]pyrimidine

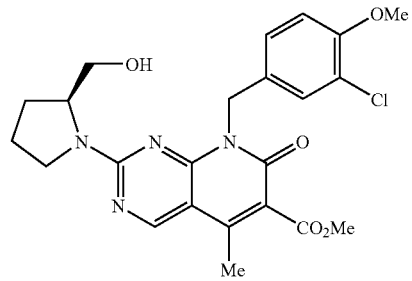

(1) A mixture of 2-methylthio-6-methoxycarbonyl-8-(3-chloro-4-methoxybenzyl)-7,8-dihydro-7-oxo-pyrido[2,3-d]pyrimidine (860 mg), m-chloroperbenzoic acid (575 mg) and chloroform (16 ml) is stirred at 0° C. for 1 hour. After addition of L-prolinol (236 mg) and triethylamine (430 mg), the mixture is stirred at 0° C. for another 1 hour. An aqueous sodium hydrogen carbonate solution is added to the mixture, and the organic layer is washed with brine and dried over sodium sulfate. Sodium sulfate is removed by filtration, and the filtrate is concentrated in vacuo. The residue is purified by column chromatography (silica gel, 50 g; solvent, hexane:ethyl acetate=1:2→ethyl acetate) to give (S)-2-(2-hydroxymethyl-1-pyrrolidinyl)-6-methoxycarbonyl-5-(3-chloro-4-methoxybenzyl)-7,8-dihydro-7-oxo-pyrido[2,3-d]pyrimidine (667 mg) as colorless crystals. M.p. 174.5° C.–176° C. MS(FAB): 459 (MH$^+$).

IR(nujol): 1695, 1614, 1510 cm$^{-1}$.

(2) To a suspension of copper cyanide (134 mg) in diethyl ether (1 ml) is added dropwise 1.1 M methyl lithium solution in diethyl ether (2.73 ml) at −78° C. The reaction mixture is stirred at 0° C. for 1 hour, and thereto is added dropwise a solution of the compound (115 mg) obtained in (1) above in tetrahydrofuran (5 ml) at −78° C. The mixture is warmed so that temperature is gradually elevated up to 0° C., and stirred at 0° C. for 1 hour. To the mixture are added a mixture of saturated aqueous ammonium chloride solution and aqueous ammonia (1:1), and chloroform, followed by stirring at room temperature for 1 hour.

The organic layer is separated, washed with brine and dried over sodium sulfate. Sodium sulfate is removed by filtration, and the filtrate is concentrated in vacuo. The residue is purified by column chromatography ($NH_2$-type, 20 g; solvent, hexane:ethyl acetate=2:1) to give (S)-2-(2-hydroxymethyl-1-pyrrolidinyl)-5-methyl-6-methoxycarbonyl-8-(3-chloro-4-methoxybenzyl)-5,6,7,8-tetrahydro-7-oxo-pyrido[2,3-d]pyrimidine (84 mg) as colorless amorphous. MS (APCI): 475 ($MH^+$).

IR(nujol): 1741, 1693, 1603 $cm^{-1}$.

(3) A mixture of the compound (10 mg) obtained in (2) above, 2,3-dichloro-5,6-dicyano-p-benzoquinone (5 mg) and dioxane (2 ml) is stirred at room temperature for 8 hours. Additional 2,2-dichloro-5,6-dicyalno-p-benzoquinone (1 mg) is added, and the mixture is stirred at room temperature for another 15 hours. Still additional 2,2-dichloro-5,6-dicyalno-p-benzoquinone (6 mg) is added, and the mixture is stirred at room temperature for 1 day and then at 60° C. for 1 day. The solvent is distilled off and the residue is purified by column chromatography (NH-type, 20 g; solvent, ethyl acetate) to give (S)-2-(2-hydroxymethyl-1-pyrrolidinyl)-5-methyl-6-methoxycarbonyl-8-(3-chloro-4-methoxybenzyl)-7,8-dihydro-7-oxo-pyrido[2,3-d]pyrimidine (3 mg) as a colorless solid. MS(APCI): 473 ($MH^+$).

IR(nujol): 1733, 1653 $cm^{-1}$.

EXAMPLE 9

(S)-1-(3-Chloro-4-methoxybenzyl)-7-(2-hydroxymethyl-1-pyrrolidinyl)-1,2-dihydro-2-oxo-1,6-naphthyridine

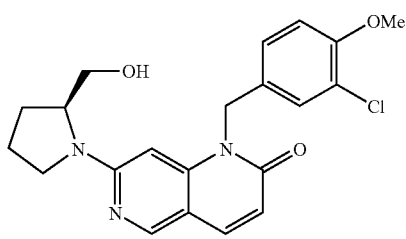

(1) To a solution of 3-ethoxycarbonyl-4-(3-chloro-4-methoxybenzylamino)-6-chloropyridine (38 mg) in tetrahydrofuran (3 ml) is added portionwise lithium aluminum hydride (8 mg) at 0° C., and the mixture is stirred at 0° C. for 30 minutes. After addition of acetone and then water, the mixture is extracted with ethyl acetate. The extract is washed with brine, and dried over sodium sulfate. Sodium sulfate is removed by filtration and the filtrate is concentrated in vacuo. The residue is purified by preparative TLC (solvent; ethyl acetate) to give 3-hydroxymethyl-4-(3-chloro-4-methoxybenzylamino)-6-chloropyridine (31 mg) as colorless crystals.

(2) A mixture of the compound (25 mg) obtained in (1) above, manganese dioxide (50 mg) and chloroform (5 ml) is stirred at room temperature for 8 hours. The mixture is filtered to remove insoluble materials and the filtrate is concentrated in vacuo to give 3-formyl-4-(3-chloro-4-methoxybenzylamino)-6-chloropyridine (26 mg) as colorless crystals. M.p. 146.5–148° C. MS(APCI): 311 ($MH^+$).

IR(nujol): 1677, 1597, 1566, 1505 $cm^{-1}$.

(3) To a solution of trimethyl phosphonoacetate (30 mg) in tetrahydrofuran (1.5 ml) is added sodium hydride (60%, 67 mg) at 0° C., and the mixture is stirred at room temperature for 1 hour. To the resulting suspension is added portionwise the compound (92 mg) obtained in (2) above at 0° C., and the mixture is stirred at 0° C. for 2 hours. After addition of ethyl acetate and water, the organic layer is washed with a saturated aqueous sodium hydrogen carbonate solution and brine, and dried over sodium sulfate. Sodium sulfate is removed by filtration, and the filtrate is concentrated in vacuo. The residue is triturated with cold diethyl ether to give 3-(methoxycarbonylvinyl)-4-(3-chloro-4-methoxybenzylamino)-6-chloropyridine (38 mg) as colorless crystals. M.p. 170–171° C. MS(APCI): 367 ($MH^+$).

IR(nujol): 1702, 1628, 1593 $cm^{-1}$.

(4) The compound (80 mg) obtained in (3) above is suspended into a solution of sodium hydride (60%, 44 mg) in methanol (5 ml) at room temperature and the mixture is refluxed for 30 minutes. After cooling, the precipitates are collected by filtration and washed with cold methanol to give 1-(3-chloro-4-methoxybenzyl)-7-chloro-1,2-dihydro-2-oxo-1,6-naphthyridine (61 mg). M.p. 208–209.5° C. MS (m/z): 335 ($MH^+$).

IR(nujol): 1665, 1573 $cm^{-1}$.

(5) A mixture of the compound (60 mg) obtained in (4) above, L-prolinol (90 mg) and N-methylpyrrolidone (3 ml) is stirred at 150° C. for 19 hours. After cooling, ethyl acetate and water are added to the mixture. The organic layer is washed with water (×3) and brine and dried over sodium sulfate. Sodium sulfate is removed by filtration and the filtrate is concentrated in vacuo. The residue is purified by preparative TLC (solvent; ethyl acetate) to give (S)-1-(3-chloro-4-methoxybenzyl)-7-(2-hydroxymethyl-1-pyrrolidinyl)-1,2-dihydro-2-oxo-1,6-naphthyridine (37 mg) as pale yellow crystals. M.p. 148–151° C.

(6) Alternatively, a mixture of 3-formyl-4-(3-chloro-4-methoxybenzylamino)-6-chloropyridine (48 mg) obtained in (2) above, L-prolinol (78 mg) and NMP (2 ml) is stirred at 100° C. for 1 day. To the mixture are added ethyl acetate and water, and the organic layer is washed with water (×3) and brine, and dried over sodium sulfate. Sodium sulfate is removed by filtration and the filtrate is concentrated in vacuo. The residue is purified by preparative TLC (solvent; chloroform:methanol=10:1) to give 3-formyl-4-(3-chloro-4-methoxybenzyl)-6-(S)-(2-hydroxymethyl-1-pyrrolidinyl)pyridine (34 mg) as pale yellow amorphous. MS(APCI): 376($MH^+$).

IR(nujol): 1641, 1608, 1565, 1503 $cm^{-1}$.

The titled compound can be obtained by treating the resultant compound in a similar manner as in steps (3) and (4) above.

EXAMPLE 10

(S)-2-(2-Hydroxymethyl-1-pyrrolidinyl)-8-(3-chloro-4-methoxybenzyl)-7,8-dihydro-7-oxo-1,8-naphthyridine

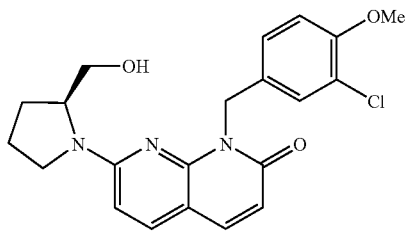

(1) A mixture of 2-chloro-5-carboxy-6-(3-chloro-4-methoxybenzylamino)pyridine (1.21 g), oxalyl chloride (0.39 ml), dimethylformamide (one drop) and methylene chloride (30 ml) is stirred at room temperature for 1.5 hours. To the mixture is added ethanol (10 ml) at 0° C., and the mixture is stirred at room temperature for 30 minutes. The solvent is distilled off and the residue is purified by column chromatography (silica gel, 40 g; solvent, chloroform:hexane=1:1) to give 2-chloro-5-ethoxycarbonyl-6-(3-chloro-4-methoxybenzylamino)pyridine (547 mg). M.p. 112.5–114° C.

(2) To a solution containing the compound (231 mg) obtained in (1) above in tetrahydrofuran (23 ml) is added portionwise lithium aluminum hydride (49 mg) at 0° C., and the mixture is stirred at 0° C. for 2 hours. Water (0.05 ml) and aqueous 10% sodium hydroxide solution (0.075 ml) at 0° C., and the mixture is stirred at room temperature for 1 hour. The mixture is filtered through sodium sulfate to remove insoluble materials, and the filtrate is concentrated in vacuo. The residue is purified by column chromatography (silica gel, 20 g; solvent, hexane:ethyl acetate=3:1) to give 2-chloro-5-hydroxymethyl-6-(3-chloro-4-methoxybenzylamino)pyridine (229 mg) as colorless oil. MS (m/z): 313 (MH$^+$)
IR(nujol): 1607, 1573, 1504 cm$^{-1}$.

(3) A mixture of the compound (196 mg) obtained in (2) above, manganese dioxide (400 mg) and chloroform (20 ml) is stirred at room temperature for 1 day. The mixture is filtered to remove insoluble materials and the filtrate is concentrated in vacuo to give 2-chloro-5-formyl-6-(3-chloro-4-methoxybenzylamino)pyridine (180 mg) as dark yellow crystals. M.p. 134.5–138.5° C. MS(APCI): 311 (MH$^+$).
IR(nujol): 1663, 1589, 1578, 1501 cm$^{-1}$.

(4) A mixture of sodium hydride (60%, 16 mg) and trimethyl 2-phosphonopropionate (73 mg) in tetrahydrofuran (3 ml) is stirred at 0° C. for 30 minutes. After addition of the compound (100 mg) obtained in (3) above, the mixture is stirred at 0° C. for 1 hour. To the mixture are added ethyl acetate and a saturated aqueous sodium hydrogen carbonate solution, and the organic layer is washed with brine and dried over sodium sulfate. Sodium sulfate is removed by filtration and the filtrate is concentrated in vacuo to give viscous yellow oil. The resultant oil is dissolved in a mixture of sodium hydride (64 mg) in methanol (7 ml) at 0° C., and the mixture is refluxed for 45 minutes. The solvent is distilled off in vacuo and the residue is purified by preparative TLC (hexane:ethyl acetate=1:1) to give 2-chloro-8-(3-chloro-4-methoxybenzylamino)-7,8-dihydro-7-oxo-1,8-naphthyridine (76 mg) as colorless crystals. M.p. 151–154.5° C. MS(APCI): 331 (MH$^+$).

(5) A mixture of the compound (69 mg) obtained in (4) above, L-prolinol (104 mg) and NMP (3 ml) is stirred at 120° C. for 17 hours. After addition of ethyl acetate and water, the organic layer is washed with water (×3) and brine, and dried over sodium sulfate. Sodium sulfate is removed by flirtation, and the filtrate is concentrated in vacuo. The residue is purified by preparative TLC (one plate, solvent; ethyl acetate) to give (S)-2-(2-hydroxymethyl-1-pyrrolidinyl)-8-(3-chloro-4-methoxybenzylamino)-7,8-dihydro-7-oxo-1,8-naphthyridine (25 mg) as a pale yellow solid. M.p. 131–134° C. MS(APCI): 400 (MH$^+$).
IR(nujol): 1645, 1605, 1578 cm$^{-1}$.

EXAMPLE 11

(S)-2-(2-Hydroxymethyl-1-pyrrolidinyl)-5-(1-methyl-2-imidazolyl)-8-(3-chloro-4-methoxybenzyl)-7,8-dihydro-7-oxo-pyrido[2,3-d]pyrimidine

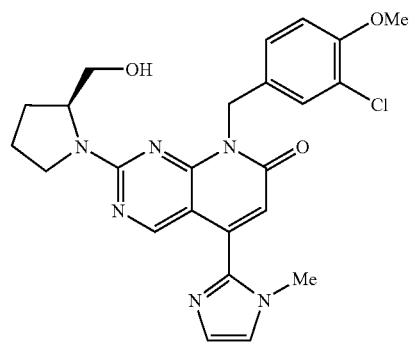

(1) A mixture of 2-methylthio-5-hydroxymethyl-4-(3-chloro-4-methoxybenzylamino)pyrimidine (9.8 g), manganese dioxide (19.6 g) and chloroform (98 ml) is stirred at room temperature for 20 hours. Manganese dioxide is removed by filtration and the filtrate is concentrated in vacuo. The residue is triturated with diisopropyl ether to give 2-methylthio-5-formyl-4-(3-chloro-4-methoxybenzylamino)pyrimidine (9.09 g) as colorless crystals. M.p. 121.5–124° C. MS(APCI): 324(MH$^+$).
IR(nujol): 1674, 1588, 1577, 1508 cm$^{-1}$.

(2) To a solution of 1-methylimidazole (243 mg) in tetrahydrofuran (6 ml) is added dropwise 1.6 M n-butyl lithium solution in hexane (1.73 ml) at −78° C., and the mixture is stirred at −78° C. for 2 hours. A solution of the compound (300 mg) obtained in (1) above in tetrahydrofuran (6 ml) is added dropwise to the mixture at −78° C., and the mixture is stirred at −78° C. for 30 minutes. After addition of a saturated aqueous sodium hydrogen carbonate solution, the mixture is warmed up to room temperature.

The mixture is extracted with chloroform. The extract is washed with brine, and dried over sodium sulfate. Sodium sulfate is removed by filtration and the filtrate is concentrated in vacuo. The residue is triturated with diethyl ether to give 2-methylthio-5-(1-methyl-2-imidazolylhydroxymethyl)-6-(3-chloro-4-methoxybenzylamino)pyrimidine (348 mg) as colorless crystals. M.p. 179–180.5° C. MS(APCI): 406 (MH$^+$).
IR(nujol): 1593, 1578 cm$^{-1}$.

(3) A mixture of the compound (340 mg) obtained in (2) above, manganese dioxide (680 mg) and chloroform (15 ml) is stirred at room temperature for 3 days. The mixture is filtered to remove insoluble substances and the filtrate is concentrated in vacuo to give 2-methylthio-5-(1-methyl-2-imidazolylcarbonyl-6-(3-chloro-4-methoxybenzylamino)pyrimidine (338 mg) as pale yellow crystals. M.p. 156–158° C. MS(APCI): 404 (MH$^+$).

IR(nujol): 1605, 1571 cm$^{-1}$.

(4) To a solution of trimethyl phosphonoacetate (85 mg) in toluene (3 ml) is added portionwise sodium hydride (60%, 19 mg) at room temperature. The mixture is stirred at room temperature for 1 hour. After addition of the compound (150 mg) obtained in (3) above, the mixture is stirred at room temperature for 1 hour, and then at 100° C. for 7 hours. A mixture of trimethyl phosphonoacetate (85 mg), sodium hydride (60%, 19 mg) and toluene (3 ml) is further added and the mixture is stirred at 100° C. for another 13 hours.

To the reaction mixture are added ethyl acetate and water. The organic layer is washed with brine and dried over sodium sulfate. Sodium sulfate is removed by filtration and the filtrate is concentrated in vacuo. The residue is purified by preparative TLC (4 plates; solvent, ethyl acetate) to give 2-methylthio-5-(1-methyl-2-imidazolyl)-8-(3-chloro-4-methoxybenzyl)-7,8-dihydro-7-oxo-pyrido[2,3-d]pyrimidine (27 mg) as colorless crystals. M.p. 218–220° C.

(5) A mixture of the compound (38 mg) obtained in (4) above, m-chloroperbenzoic acid (26 mg) and chloroform (3 ml) is stirred at 0° C. for 1 hour. After addition of prolinol (45 mg), the mixture is stirred at room temperature for 1 hour. To the reaction mixture is added a saturated aqueous sodium hydrogen carbonate solution. The organic layer is washed with brine, and dried over sodium sulfate. Sodium sulfate is removed by filtration and the filtrate is concentrated in vacuo. The residue is purified by preparative TLC (solvent, ethyl acetate:methanol=4:1) to give (S)-2-(2-hydroxymethyl-1-pyrrolidinyl)-5-(1-methyl-2-imidazolyl)-8-(3-chloro-4-methoxybenzyl)-7,8-dihydro-7-oxo-pyrido[2,3-d]pyrimidine (41 mg) as colorless powder. MS(APCI): 481 (MH$^+$).

IR(nujol): 1655, 1582, 1533 cm$^{-1}$.

EXAMPLE 12

(S)-2-(2-Hydroxymethyl-1-pyrrolidinyl)-5-(2-pyridyl)-8-(3-chloro-4-methoxybenzyl)-7,8-dihydro-7-oxo-pyrido[2,3-d]pyrimidine

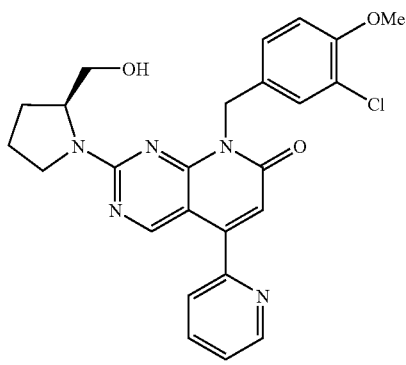

(1) A 1.6 M n-butyl lithium solution in hexane (3.54 ml) is added to diethyl ether (10 ml) at −78° C. To the mixture is added dropwise 2-bromopyridine (0.556 ml) at −78° C. over 7 minutes. The mixture is stirred at −78° C. for 20 minutes.

To the mixture is added dropwise a solution of (S)-2-(2-hydroxymethyl-1-pyrrolidinyl)-5-formyl-4-(3-chloro-4-methoxybenzylamino)pyrimidine (314 mg) in tetrahydrofuran (10 ml) at −78° C., and the mixture is stirred at −78° C. for another 30 minutes. After addition of aqueous sodium hydrogen carbonate solution, the mixture is warmed to room temperature and extracted with ethyl acetate. The organic layer is washed with brine, and dried over sodium sulfate. Sodium sulfate is removed by filtration and the filtrate is concentrated in vacuo to give (S)-2-(2-hydroxymethyl-1-pyrrolidinyl)-5-(2-pyridylhydroxymethyl)-6-(3-chloro-4-methoxybenzyl)pyrimidine as brown amorphous. The brown amorphous is then stirred at room temperature for 15 hours in the presence of manganese dioxide (0.90 g) and chloroform (15 ml) at room temperature for 15 hours. Manganese dioxide is removed by filtration, and the filtrate is concentrated in vacuo. The residue is purified by column chromatography (silica gel, 40 g; solvent, ethyl acetate: chloroform=1:1→ethyl acetate alone) and preparative TLC (solvent; ethyl acetate) to give (S)-2-(2-hydroxymethyl-1-pyrrolidinyl)-5-(2-pyridylcarbonyl)-6-(3-chloro-4-methoxybenzylamino)pyrimidine (216 mg) as pale yellow amorphous. MS(APCI): 454 (MH$^+$).

IR(neat): 1591, 1566, 1524 cm$^{-1}$.

(2) A mixture of sodium hydride (60%, 36 mg) and trimethyl phosphonoacetate (70 mg) in toluene (10 ml) is stirred at room temperature for 1 hour. After addition of the compound (116 mg) obtained in (1) above, the mixture is stirred at 100° C. for 6 hours. To the mixture is added ethyl acetate and water, and the organic layer is washed with brine and dried over sodium sulfate. Sodium sulfate is removed by filtration and the filtrate is concentrated in vacuo. The residue is purified by preparative TLC (solvent; ethyl acetate (×2)) to give (S)-2-(2-hydroxymethyl-1-pyrrolidinyl)-5-(2-pyridyl)-8-(3-chloro-4-methoxybenzyl)-7,8-dihydro-7-oxo-pyrido[2,3-d]pyrimidine (21 mg). M.p. 183.5–186.5° C. MS(APCI): 478 (MH$^+$).

IR(nujol): 1644, 1572, 1533 cm$^{-1}$.

EXAMPLE 13

(S)-2-(2-Hydroxymethyl-1-pyrrolidinyl)-5-(1-methyl-2-imidazolyl)-6-methoxycarbonyl-8-(3-chloro-4-methoxybenzyl)-7,8-dihydro-7-oxo-pyrido[2,3-d]pyrimidine

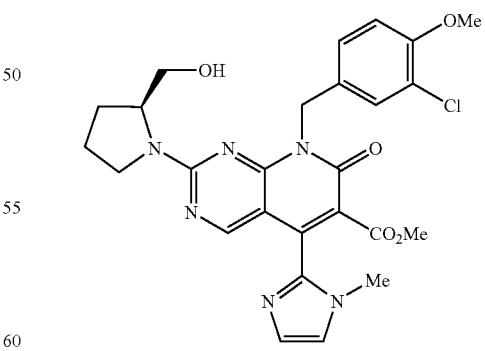

(1) To ice-salt cooled tetrahydrofuran solution is added a solution of titanium tetrachloride (331 mg) in chloroform (993 mg) under argon atmosphere. The mixture is stirred at the same temperature for 30 minutes. To the mixture are added dimethyl malonate (69 mg) and then 2-methylthio-5-(1-methyl-2-imidazolylcarbonyl)-6-(3-chloro-4-methoxybenzylamino)pyrimidine (141 mg). A solution of pyridine (220 mg) in tetrahydrofuran (1 ml) is added dropwise to the solution of ice-salt-cooled mixture, and the mixture is stirred at the same temperature for 30 minutes. After addition of tetrahydrofuran (3 ml), the mixture is stirred at room temperature for 5 hours. To the mixture are added ethyl acetate and sodium hydrogen carbonate at 0° C. and the insoluble materials are removed by filtration on celite. The organic layer is separated, washed with brine and dried over sodium sulfate. Sodium sulfate is removed by filtration and the filtrate is concentrated in vacuo. The residue is triturated with methanol to give 2-methylthio-5-(1-mehyl-2-imidazolyl)-6-methoxycarbonyl-8-(3-chloro-4-methoxybenzyl)-7,8-dihydro-7-oxo-pyrido[2,3-d]pyrimidine (109 mg) as a yellow solid. MS(APCI): 486 (MH$^+$).

(2) A mixture of the compound (103 mg) obtained in (1) above and m-chloroperbenzoic acid (63 mg) in chloroform (3 ml) is stirred at room temperature for 30 minutes. After addition of prolinol (107 mg) and triethylamine (108 mg), the mixture is stirred at room temperature for 15 hours. An aqueous sodium hydrogen carbonate solution is added to the mixture, and the organic layer is separated, washed with brine and dried over sodium sulfate. Sodium sulfate is removed by filtration and the filtrate is dried in vacuo. The residue is purified by column chromatography (silica gel, 15 g; solvent, ethyl acetate→ethyl acetate:methanol=5:1) and preparative TLC (solvent; ethyl acetate:methanol=10:1) to give (S)-2-(2-hydroxymethyl-1-pyrrolidinyl)-5-(1-methyl-2-imidazolyl)-6-methoxycarbonyl-8-(3-chloro-4-methoxybenzyl)-7,8-dihydro-7-oxo-pyrido[2,3-d]pyrimidine (120 mg) as a pale yellow solid. M.p. 142–145° C. MS(APCI): 539 (MH$^+$). IR(nujol): 1734, 1657, 1597, 1588, 1549, 1503 cm$^{-1}$.

EXAMPLE 14

(S)-2-(2-Hydroxymethyl-1-pyrrolidinyl)-5-[2-(4-morpholinyl)ethyl]-8-(3-chloro-4-methoxybenzyl)-7,8-dihydro-7-oxo-pyrido[2,3-d]pyrimidine

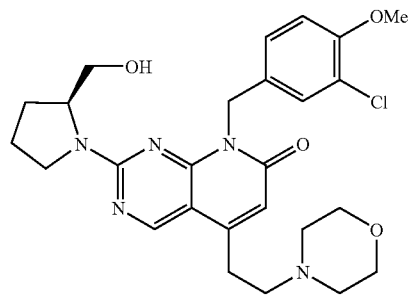

(1) Several pieces of iodine is added to a suspension of magnesium (11.0 g) in tetrahydrofuran (350 ml), and the mixture is stirred until red color fades out. To the mixture is added a tetrahydrofuran (100 ml) solution containing vinyl bromide (25 ml) corresponding to one tenth volume of said mixture. The resulting mixture is heated until the reaction takes place and refluxed gently. A solution of vinyl bromide in tetrahydrofuran is added dropwise at such a rate that a moderate reflux is maintained. After the addition is completed, the mixture is refluxed for another 30 minutes. The insoluble materials are removed by decantation to give a 1N tetrahydrofuran solution of vinyl magnesium bromide.

A solution of (S)-2-(2-hydroxymethyl-1-pyrrolidinyl)-5-formyl-4-(3-chloro-4-methoxybenzylamino)pyrimidine (4.1 g) in tetrahydrofuran (30 ml) is added to a solution of vinyl magnesium bromide in tetrahydrofuran (43.5 ml) at 0° C., and the mixture is stirred at 0° C. for 1 hour. To the mixture is added a saturated aqueous ammonium chloride solution, and the mixture is extracted with ethyl acetate. The extract is washed with water and then brine, and dried over sodium sulfate. Sodium sulfate is removed by filtration, and the filtrate is concentrated in vacuo. The residue is purified by column chromatography (silica gel, 100 g; ethyl acetate→ethyl acetate:methanol=20:1, and then silica gel, 50 g; chloroform:methanol=50:1) to give (S)-2-(2-hydroxymethyl-1-pyrrolidinyl)-5-(1-hydroxymethyl-2-propen-1-yl)-4-(3-chloro-4-methoxybenzylamino)pyrimidine (2.70 g) as colorless amorphous. MS(APCI): 405 (MH$^+$).

IR(nujol): 1606, 1575 cm$^{-1}$.

(2) A mixture of the compound (2.70 g) obtained in (1) above, manganese dioxide (8.1 g) and chloroform (120 ml) is stirred at room temperature for 15 hours. The mixture is filtered to remove insoluble materials and the filtrate is concentrated in vacuo. The residue is purified by column chromatography (silica gel, 90 g; chloroform:ethyl acetate=2:1), and triturated with cold diethyl ether to give (S)-2-(2-hydroxymethyl-1-pyrrolidinyl)-5-vinylcarbonyl-4-(3-chloro-4-methoxybenzylamino)pyrimidine (1.92 g) as pale yellow crystals. M.p. 118–121.5° C. MS (m/z): 403 (MH$^+$).

IR(nujol): 1639, 1603, 1521 cm$^{-1}$.

(3) A mixture of the compound (300 mg) obtained in (2) above, morpholine (324 mg) and ethanol (10 ml) is stirred at room temperature for 1 hour. The solvent is distilled off, and the residue is diluted with ethyl acetate and washed with water (×3) and brine, and dried over sodium sulfate. Sodium sulfate is removed by filtration and the filtrate is concentrated in vacuo to give (S)-2-(2-hydroxymethyl-1-pyrrolidinyl)-5-(2-(4-morpholinyl)ethylcarbonyl)-4-(3-chloro-4-methoxybenzylamino)pyrimidine (358 mg) as colorless amorphous. MS(APCI): 490 (MH$^+$).

IR(neat): 1625, 1593, 1525 cm$^{-1}$.

(4) A 1.6M solution of n-butyl lithium in hexane (1.76 ml) is added to a mixture of dicyclohexylamine (510 mg) in tetrahydrofuran (3 ml) at −78° C., and the mixture is stirred at −78° C. After addition of methyl trimethylsilyl acetate (462 µl), the whole reaction solution is stirred at −78° C. for 10 minutes. To the mixture is added dropwise a solution of the compound (138 mg) obtained in (3) above in tetrahydrofuran at −78° C., and the mixture is stirred at 0° C. for 5 hours, and then at room temperature for 15 hours. After addition of water and ethyl acetate, the organic layer is separated, washed with brine, and dried over sodium sulfate.

Sodium sulfate is removed by filtration and the filtrate is concentrated in vacuo. The residue is purified by column chromatography (NH-type, 25 g; solvent, ethyl acetate) and preparative TLC (aluminium oxide; solvent, ethyl acetate (×3)) to give ((S)-2-(2-hydroxymethyl-1-pyrrolidinyl)-5-[2-(4-morpholinyl)ethyl]-8-(3-chloro-4-methoxybenzyl)-7,8-dihydro-7-oxo-pyrido[2,3-d]pyrimidine (11 mg) as colorless amorphous. MS(APCI): 514 (MH$^+$).

IR (nujol): 1583 cm$^{-1}$.

EXAMPLES 15–42

The corresponding starting materials are treated in the same manner as described in the Examples above to give the compounds as listed in the following Table 1.

TABLE 1

| Ex. No. | Chemical structure | Physicochemical properties etc. |
|---|---|---|
| (No. 1) | | |
| 15 | 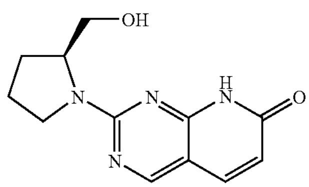 | M.p. 99–103° C.<br>MS (m/z): 247 (MH⁺) |
| 16 | 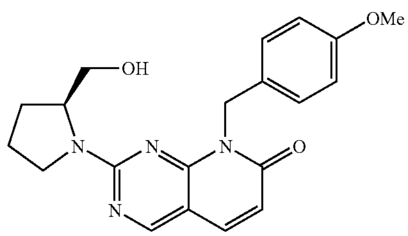 | M.p. 135–136° C. |
| 17 | 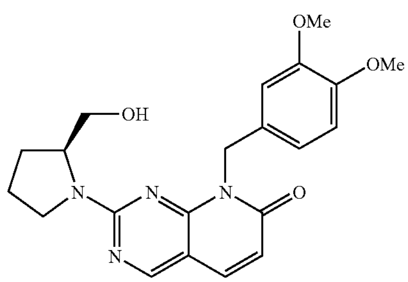 | M.p. 132° C. |
| (No. 2) | | |
| 18 | 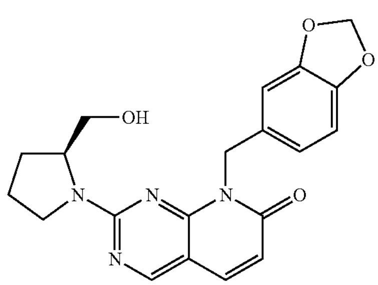 | M.p. 154–155° C. |
| 19 | 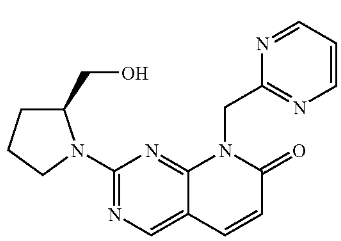 | M.p. 150–151° C. |
| 20 | 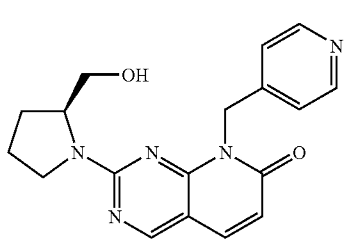 | M.p. 143–144° C. |

TABLE 1-continued

| Ex. No. | Chemical structure | Physicochemical properties etc. |
|---|---|---|
| 21 | 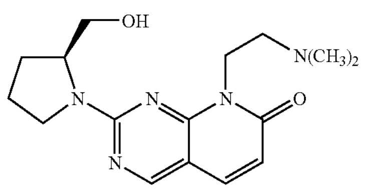 | M.p. 102–104° C. |
| 22 | 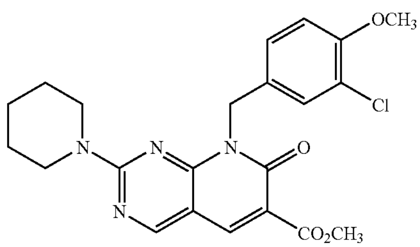 | M.p. 201–203° C.<br>MS (m/z): 443 (MH$^+$) |
| 23 | 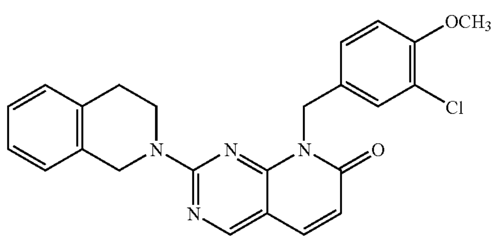 | M.p. 167–168° C. |
| 24 | 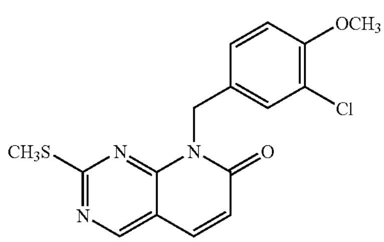 | M.p. 189–190° C. |

(No. 3)

| | | |
|---|---|---|
| 25 | | M.p. 172–173° C. |
| 26 | | M.p. 139–141° C. |

TABLE 1-continued

| Ex. No. | Chemical structure | Physicochemical properties etc. |
|---|---|---|
| 27 | 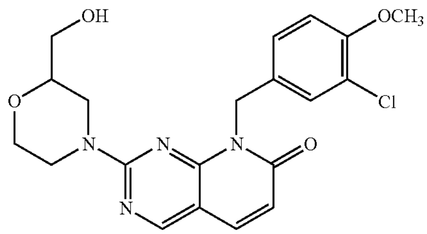 | M.p. 207–209° C. |
| 28 | 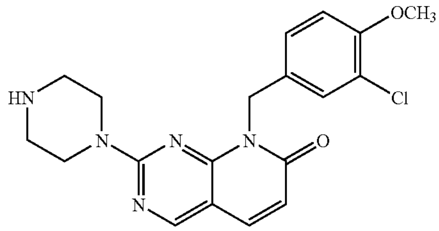 | M.p. 169.5–170° C. |
| 29 | 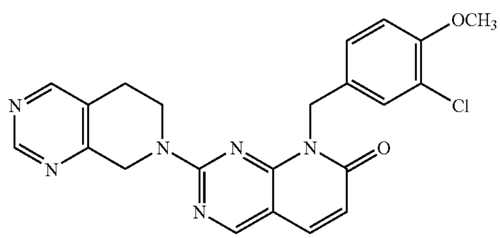 | M.p. 200–201° C. |
| 30 | 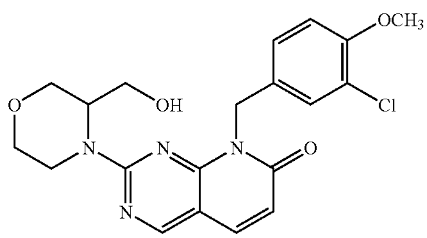 | Amorphous MS (m/z): 417 (MH+) |

(No. 4)

| Ex. No. | Chemical structure | Physicochemical properties etc. |
|---|---|---|
| 31 | | M.p. 234–242° C. |
| 32 | | M.p. 158–159° C. |

TABLE 1-continued

| Ex. No. | Chemical structure | Physicochemical properties etc. |
|---|---|---|
| 33 | 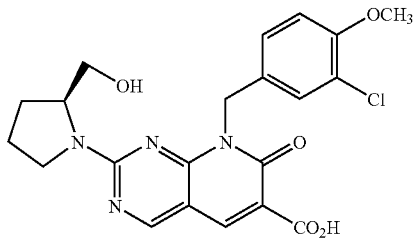 | M.p. 258–264° C. |
| 34 | 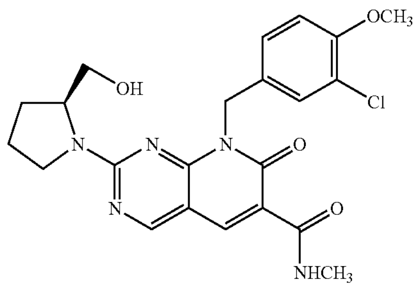 | M.p. 191–191.5° C. |
| 35 | 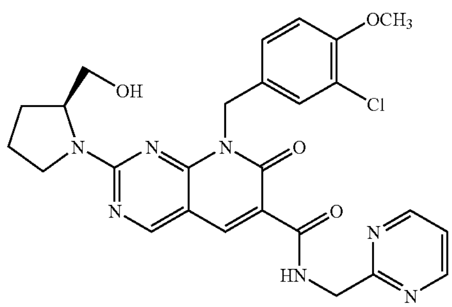 | M.p. 216–218° C. |
| 36 | 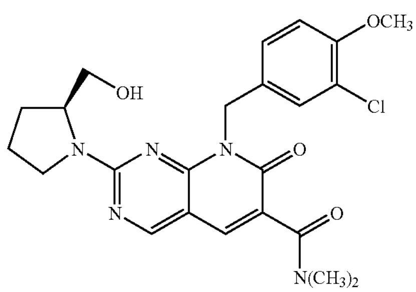 | Amorphous<br>MS (m/z): 472<br>(MH+) |

(No. 5)

| 37 | | Oil<br>MS (m/z): 527<br>(MH+) |

TABLE 1-continued

| Ex. No. | Chemical structure | Physicochemical properties etc. |
|---|---|---|
| 38 | 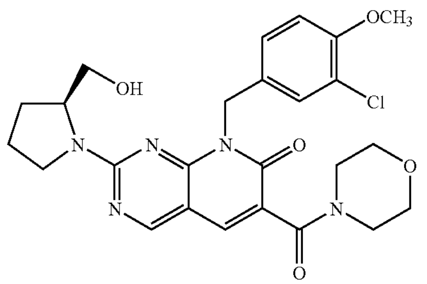 | Amorphous<br>MS (m/z): 514 (MH+) |
| 39 | 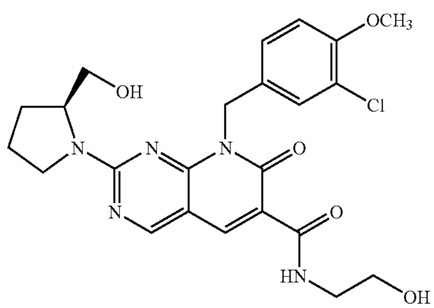 | M.p. 207–210° C. |
| 40 | 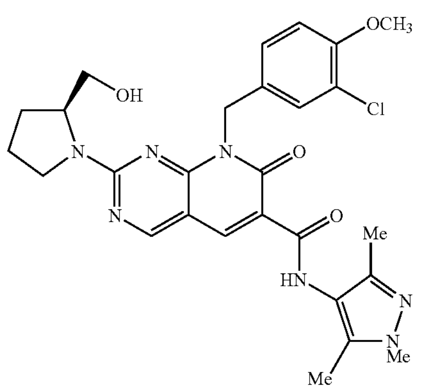 | Powder<br>MS (m/z) 552 (MH+) |
| 41 | 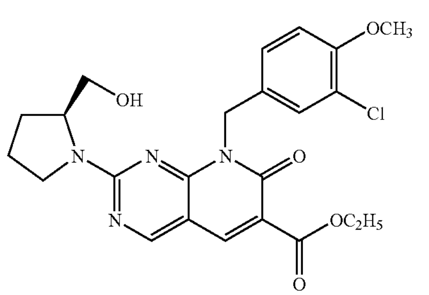 | Amorphous<br>MS (m/z): 473 (MH+) |

TABLE 1-continued

| Ex. No. | Chemical structure | Physicochemical properties etc. |
|---|---|---|
| (No. 6) | | |
| 42 | (structure) | M.p. 199–201° C. |

REFERENCE EXAMPLE 1

(1) A mixture of 3-ethoxycarbonyl-4-hydroxy-6-oxopyridine (7.80 g) and phosphoryl chloride (48 ml) is stirred at 100° C. for 8 hours. The excess of phosphoryl chloride is removed under reduced pressure and the residue is poured into ice-cold water. The mixture is basified with sodium carbonate and extracted with ethyl acetate. The extract is washed with water and then brine, and dried over sodium sulfate. Sodium sulfate is removed by filtration and the filtrate is concentrated in vacuo. The residue is purified by column chromatography (silica gel, 100 g; solvent, hexane:ethyl acetate=10:1) to give 2,4-dichloro-5-ethoxycarbonylpyridine (8.50 g) as colorless crystals. M.p. 32–32.5° C. MS (m/z): 220 (MH$^+$).

(2) A mixture of the compound (1.02 g) obtained in (1) above, 3-chloro-4-methoxybenzylamine (1.02 g), triethylamine (823 mg) and acetonitrile (20 ml) is stirred at room temperature for 1.5 days, followed by reflux for 3 hours. The solvent is distilled off and the residue is diluted with a mixed solvent of ethyl acetate and an aqueous sodium hydrogen carbonate solution. The organic layer is washed with a saturated aqueous sodium hydrogen carbonate solution, water and brine, and dried over sodium sulfate. Sodium sulfate is removed by filtration and the filtrate is concentrated in vacuo. The residue is purified by column chromatography (silica gel, 25 g; solvent, hexane:ethyl acetate=4:1), and triturated with cold-diethyl ether to give 3-ethoxycarbonyl-6-chloro-4-(3-chloro-4-methoxybenzylamino)pyridine (1.17 g) as colorless crystals. M.p. 115.5–117.5° C. MS (m/z): 355(MH$^+$).

REFERENCE EXAMPLE 2

(1) To a mixture of diisopropylamine (3.76 g) in tetrahydrofuran (25 ml) is added dropwise n-butyl lithium (23.2 ml) at −78° C. The mixture is stirred at 0° C. for 10 minutes. A solution of 2,6-dichloropyridine (5.0 g) in tetrahydrofuran (25 ml) is then added dropwise at −78° C. over 20 minutes. The mixture is stirred at −78° C. for 3 hours, poured into powdered dry ice, and the resultant mixture is allowed to stand overnight at room temperature.

The solvent is distilled off and the residue is dissolved in a mixed solvent of ethyl acetate and an aqueous 10% sodium hydroxide solution. The aqueous layer is separated and acidified with concentrated hydrochloric acid. The resulting colorless precipitates are collected by filtration and washed with cold water to give 2,6-dichloronicotic acid (4.50 g). M.p. 148–150° C. MS(ESI): 190 (M−H)$^-$.

(2) A mixture of the compound (500 mg) obtained in (1) above, 3-chloro-4-methoxybenzylamine (638 mg), potassium carbonate (817 mg), copper bromide (313 mg) and 1-methyl-2-pyrrolidinone (10 ml) is stirred at 120° C. for 2.5 hours. After the mixture is cooled to room temperature, a mixture of ethyl acetate and aqueous 1N hydrochloric acid solution is added to the mixture. The organic layer is separated and washed with water (×2) and brine, and dried over sodium sulfate. Sodium sulfate is removed by filtration and the filtrate is concentrated in vacuo. The residue is purified by column chromatography (silica gel, 30 g; solvent, chloroform→chloroform:methanol=70:1) to give 2-(3-chloro-4-methoxybenzylamino)-6-chloronicotic acid (471 mg) as colorless crystals. M.p. 184–185.5° C. MS (m/z): 325 (M−H)$^-$.

INDUSTRIAL APPLICABILITY

The compound (I) of the present invention and a pharmaceutically acceptable salt thereof exhibit excellent PDE V inhibitory activities, and they are useful pharmaceutical compounds for the prophylaxis or treatment of penile erectile dysfunction, etc.

The invention claimed is:

1. A pyridopyrimidine or a naphthyridine compound of the formula (I):

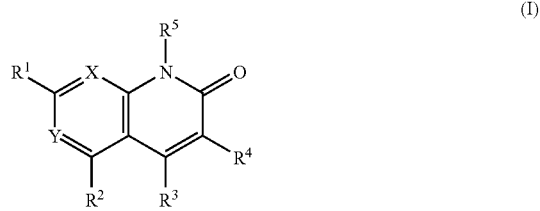

wherein $R^1$ is a nitrogen-containing heterocyclic group which is optionally substituted by (i) a lower alkyl group optionally substituted by a group selected from the group consisting of a hydroxy group, a halogen atom and a lower alkoxy group;
(ii) an amino group which is optionally substituted by a group selected from the group consisting of a lower alkyl group optionally substituted by a heteroaryl group, a lower alkyl group optionally substituted by an aryl group, and a lower alkoxy group; or
(iii) an alkoxy group which is optionally substituted by (1) an aryl group optionally substituted by a group selected from the group consisting of a hydroxy group, a halogen atom and a lower alkoxy group, or (2) a lower alkyl group optionally substituted by a heteroaryl group which may be optionally substituted by a group selected from the group consisting of a hydroxy group, a halogen atom and a lower alkoxy group;

$R^2$ is a hydrogen atom or a lower alkyl group;

$R^3$ is (i) a hydrogen atom; (ii) a lower alkyl group which is optionally substituted by a nitrogen-containing heterocyclic group; or (iii) a heteroaryl group which is optionally substituted by a group selected from the group consisting of a hydroxy group, a halogen atom and a lower alkoxy group;

$R^4$ is (i) a hydrogen atom; (ii) a lower alkyl group; (iii) a carboxyl group esterified with a lower alkyl group; (iv) a carboxyl group amidated with a lower alkyl-substituted amino group which may be optionally substituted by a hydroxy group or a 5- to 6-membered nitrogen-containing heteromonocyclic group optionally substituted by a lower alkyl group; or (v) a carboxyl group amidated with a 5- to 6-membered nitrogen-containing heteromonocyclic group optionally substituted by a lower alkyl group;

$R^5$ is a lower alkyl group which may be optionally substituted by a group selected from the group consisting of (i) an aryl group optionally substituted by a group selected from the group consisting of a hydroxy group, a halogen atom and a lower alkoxy group;
(ii) a heteroaryl group optionally substituted by a group selected from the group consisting of a hydroxy group, a halogen atom and a lower alkoxy group; and
(iii) a di-lower alkylamino group; and X is a group of the formula: =CH— and Y is a nitrogen atom, or X and Y are both nitrogen atoms, or a pharmaceutically acceptable salt thereof.

2. The compound according to claim 1, wherein X and Y are both nitrogen atoms.

3. The compound according to claim 2, wherein the nitrogen-containing heterocyclic group for $R^1$ is a 5- or 6-membered nitrogen-containing heteromonocyclic group or a 8- to 10-membered nitrogen-containing heterobicyclic group, the aryl group for $R^5$ is a phenyl group and the heteroaryl group for $R^5$ is a pyridyl group or pyrimidyl group.

4. The compound according to claim 3, wherein $R^5$ is a lower alkyl group which may be optionally substituted by a phenyl group optionally substituted by a group selected from the group consisting of a lower alkoxy group, a lower alkylenedioxy group and a halogen atom, a pyridyl group or a pyrimidyl group, which groups are optionally substituted by a group selected from the group consisting of a lower alkoxy group and/or a halogen atom and a di-lower alkylamino group.

5. The compound according to claim 4, wherein the nitrogen-containing heterocyclic group for $R^1$ is a 5- or 6-membered nitrogen-containing heteromonocyclic group selected from the group consisting of a pyrrolyl group, an oxazolyl group, a pyrazolyl group, a pyrrolinyl group, a pyrrolidinyl group, an imidazolyl group, a piperidyl group, a piperazinyl group, a morpholinyl group, a pyridyl group, a pyridazinyl group, a pyrimidinyl group, a pyrazinyl group and a triazinyl group, or an 8- to 10-membered nitrogen-containing heterobicyclic group selected from the group consisting of an indolyl group, an isoindolyl group, an indolydinyl group, a quinolyl group, an isoquinolyl group and a purinyl group; and the amidated carboxyl group for $R^4$ is a carboxyl group amidated with a lower alkyl-substituted amino group optionally substituted by a 5- to 6-membered nitrogen-containing heteromonocyclic group selected from the group consisting of a pyrrolyl group, an oxazolyl group, a pyrazolyl group, a pyrrolinyl group, a pyrrolidinyl group, an imidazolyl group, a piperidyl group, a piperazinyl group, a morpholinyl group, a pyridyl group, a pyridazinyl group, a pyrimidinyl group, a pyrazinyl group, a triazinyl group, an imidazolidinyl group and a thiazolyl group, each group being optionally substituted by a lower alkyl group, or a carboxyl group amidated with a 5- to 6-membered nitrogen-containing heteromonocyclic group selected from the group consisting of a pyrrolyl group, an oxazotyl group, a pyrazolyl group, a pyrrolinyl group, a pyrrolidinyl group, an imidazolyl group, a piperidyl group, a piperazinyl group, a morpholinyl group, a pyridyl group, a pyridazinyl group, a pyrimidinyl group, a pyrazinyl group, a triazinyl group, an imidazolidinyl group and a thiazolyl group, each group being optionally substituted by a lower alkyl group.

6. The compound according to claim 5, wherein the nitrogen-containing heterocyclic group for $R^1$ is a 5- or 6-membered nitrogen-containing heteromonocyclic group of the formula:

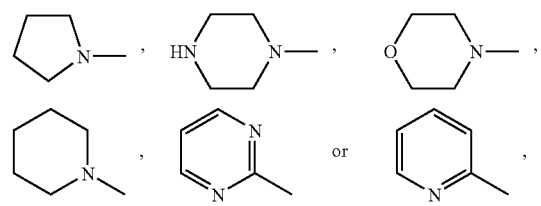

or a 8- to 10-membered nitrogen-containing heterobicyclic group of the formula:

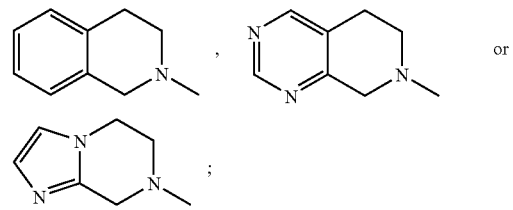

$R^4$ is a hydrogen atom, a lower alkyl group or a carboxyl group amidated with a group selected from the group consisting of a lower alkyl-substituted amino group which may be optionally substituted by a group of the formula:

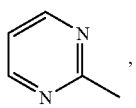

an amino group optionally substituted by a group of the formula:

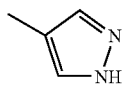

which may be optionally substituted by a lower alkyl group, and a group of the formula:

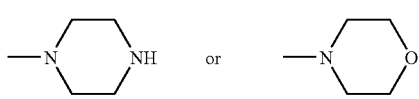

which may be optionally substitute by a lower alkyl group.

7. The compound according to claim 6, wherein the nitrogen-containing heterocyclic group, which is optionally substituted by a lower alkyl group optionally substituted by a group selected from the group consisting of a hydroxy group, a halogen atom and a lower alkoxy group, for $R^1$ is a group of the formula:

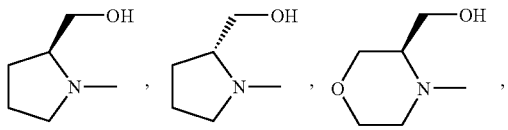

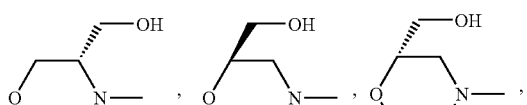

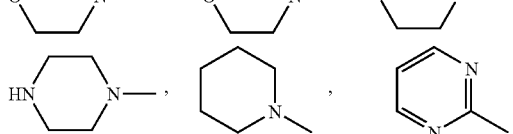

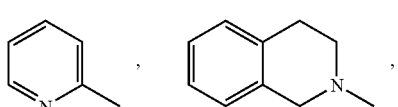

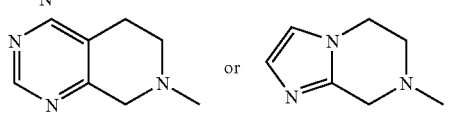

$R^4$ is a hydrogen atom, a lower alkyl group or a carboxyl group amidated with a group selected from the group consisting of a lower alkyl-substituted amino group optionally substituted by a group of the formula:

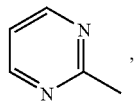

an amino group optionally substituted by a group of the formula:

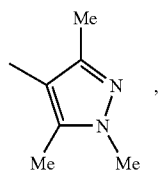

a group of the formula:

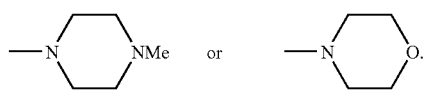

8. The compound according to claim 7, wherein $R^1$ is a group of the formula:

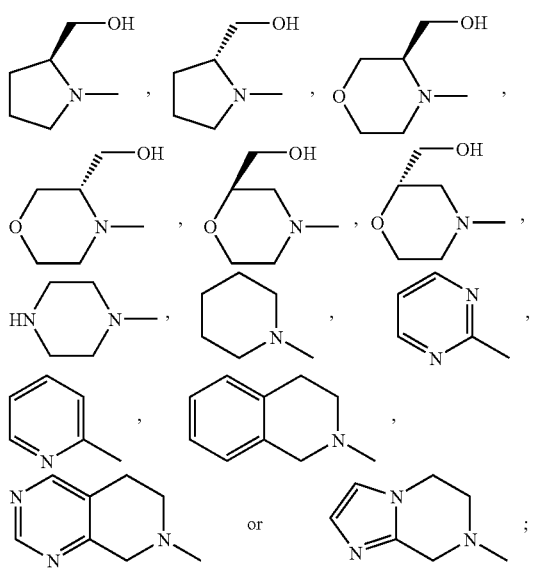

$R^2$ is a hydrogen atom;
$R^3$ is a hydrogen atom;
$R^4$ is a hydroxy group or a carboxyl group amidated with a lower alkyl-substituted amino group optionally substituted by a group of the formula:

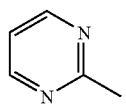

an amino group optionally substituted by a group of the formula:

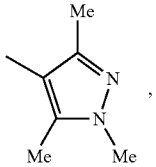

R⁵ is a lower alkyl group substituted by a phenyl group optionally substituted by a lower alkoxy group and/or a halogen atom.

9. The compound according to claim 8, wherein R¹ is a group of the formula:

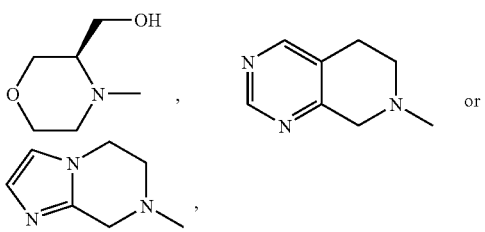

R⁴ is a carboxyl group amidated with a lower alkyl-substituted amino group optionally substituted by a group of the formula:

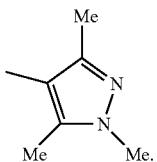

10. (S)-2-(2-Hydroxymethyl-1-pyrrolidinyl)-5-[2-(4-morpholinyl)ethyl]-8-(3-chloro-4-methoxybenzyl)-7,8-dihydro-7-oxo-pyrido[2,3-d]pyrimidine;

(S)-2-(2-hydroxymethyl-1-pyrrolidinyl)-6-[N-{4-(1,3,5-trimethyl)pyrazolyl}carbamoyl]-8-(3-chloro-4-methoxybenzyl)-7,8-dihydro-7-oxo-pyrido[2,3-d]pyrimidine;

(S)-2-(2-hydroxymethyl-1-pyrrolidinyl)-8-(3-chloro-4-methoxybenzyl)-7,8-dihydro-7-oxo-pyrido[2,3-d]pyrimidine;

(S)-2-(2-hydroxymethyl-1-pyrrolidinyl)-5-methyl-8-(3-chloro-4-methoxybenzyl)-7,8-dihydro-7-oxo-pyrido[2,3-d]pyrimidine;

or a pharmaceutically acceptable salt thereof.

11. (S)-2-(2-hydroxymethyl-1-pyrrolidinyl)-6-[N-{4-(1,3,5-trimethyl)pyrazolyl}carbamoyl]-8-(3-chloro-4-methoxybenzyl)-7,8-dihydro-7-oxo-pyrido[2,3-d]pyrimidine, or a pharmaceutically acceptable salt thereof.

12. A pyridopyrimidine or a naphthyridine compound of the formula (VIII):

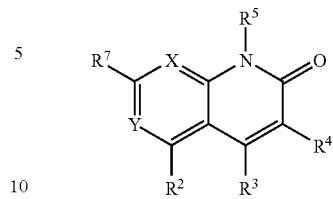

wherein R⁷ is a halogen atom or a group of the formula:
—SR⁹ wherein R⁹ is a lower alkyl group or a phenyl group which may be optionally substituted by a group selected from the group consisting of a lower alkyl group, a hydroxy group, a halogen atom and a lower alkoxy group;

R² is a hydrogen atom or a lower alkyl group;

R³ is (i) a hydrogen atom; (ii) a lower alkyl group which is optionally substituted by a nitrogen-containing heterocyclic group; or (iii) a heteroaryl group which is optionally substituted by a group selected from the group consisting of a hydroxy group, a halogen atom and a lower alkoxy group, R⁴ is (i) a hydrogen atom; (ii) a lower alkyl group; (iii) a carboxyl group esterified with a lower alkyl group; (iv) a carboxyl group amidated with a lower alkyl-substituted amino group which may be optionally substituted by a hydroxy group or a 5- to 6-membered nitrogen-containing heteromonocyclic group optionally substituted by a lower alkyl group; or (v) a carboxyl group amidated with a 5- to 6-membered nitrogen-containing heteromonocyclic group optionally substituted by a lower alkyl group, R⁵ is a lower alkyl group which may be optionally substituted by a group selected from the group consisting of (i) an aryl group optionally substituted by a group selected from the group consisting of a hydroxy group, a halogen atom and a lower alkoxy group;
(ii) a heteroaryl group optionally substituted by a group selected from a hydroxy group, a halogen atom and a lower alkoxy group; and
(iii) a di-lower alkylamino group; and is a group of the formula: =CH—Y is a nitrogen atom, or X and Y are both nitrogen atoms, or a salt thereof.

13. A compound of the formula:

or a salt thereof.

14. A pharmaceutical composition, which contains as an active ingredient a compound as set forth in any one of claims 1–13 or a pharmaceutically acceptable salt thereof.

15. A method for the treatment of penile erectile dysfunction, which comprises administering to a patient in need thereof an effective amount of a compound as set forth in any one of claims 1–13 or a pharmaceutically acceptable salt thereof.

* * * * *

UNITED STATES PATENT AND TRADEMARK OFFICE
CERTIFICATE OF CORRECTION

PATENT NO. : 7,078,522 B2
APPLICATION NO. : 10/647234
DATED : July 18, 2006
INVENTOR(S) : Koichiro Yamada et al.

It is certified that error appears in the above-identified patent and that said Letters Patent is hereby corrected as shown below:

In claim 5, column 54, line 25, "oxazotyl" should read --oxazolyl--.

In claim 6, column 54, line 59, after ";", insert --and--.

In claim 6, column 55, line 30, "substitute" should read --substituted--.

In claim 7, column 56, line 15, after ",", insert --and--.

In claim 8, column 56, line 65, after the formula, insert --or--.

In claim 8, column 57, line 8, after ",", insert --and--.

In claim 9, column 57, line 28, after ",", insert --and--.

In claim 14, column 58, line 60, "1-13 or" should read --1-13, or--.

In claim 15, column 58, line 64, "1-13 or" should read --1-13, or--.

Signed and Sealed this

Twenty-third Day of January, 2007

JON W. DUDAS
*Director of the United States Patent and Trademark Office*